United States Patent
Sandig et al.

(10) Patent No.: US 9,163,089 B2
(45) Date of Patent: Oct. 20, 2015

(54) ENHANCEMENT OF PROTEIN PRODUCTION YIELD MEDIATED BY A FAST SHUTTLING CDC42 GTPASE

(75) Inventors: Volker Sandig, Berlin (DE); Karsten Winkler, Berlin (DE); Henning Von Horsten, Berlin (DE); Thomas Rose, Blankenfelde (DE)

(73) Assignee: Probiogen AG, Berlin (DE)

( * ) Notice: Subject to any disclaimer, the term of this patent is extended or adjusted under 35 U.S.C. 154(b) by 79 days.

(21) Appl. No.: 14/117,005

(22) PCT Filed: May 14, 2012

(86) PCT No.: PCT/EP2012/058881
§ 371 (c)(1),
(2), (4) Date: Jan. 22, 2014

(87) PCT Pub. No.: WO2012/152945
PCT Pub. Date: Nov. 15, 2012

(65) Prior Publication Data
US 2014/0377803 A1    Dec. 25, 2014

Related U.S. Application Data

(60) Provisional application No. 61/485,286, filed on May 12, 2011.

(51) Int. Cl.
| | | |
|---|---|---|
| C07K 14/47 | (2006.01) | |
| C07K 16/30 | (2006.01) | |
| C12N 15/67 | (2006.01) | |
| C12N 5/00 | (2006.01) | |
| C07K 14/005 | (2006.01) | |
| C07K 16/32 | (2006.01) | |
| C07K 16/18 | (2006.01) | |

(52) U.S. Cl.
CPC ........... *C07K 16/3015* (2013.01); *C07K 14/005* (2013.01); *C07K 14/4702* (2013.01); *C07K 16/18* (2013.01); *C07K 16/32* (2013.01); *C12N 5/00* (2013.01); *C12N 15/67* (2013.01); *C12N 2501/405* (2013.01); *C12N 2510/02* (2013.01); *C12N 2710/10322* (2013.01)

(58) Field of Classification Search
CPC ...................... C12N 2501/405; C07K 14/4702
See application file for complete search history.

(56) References Cited

FOREIGN PATENT DOCUMENTS

WO    2009023760    *   2/2009

OTHER PUBLICATIONS

Adenovirus E1B. 2015. On the web at en.wikipedia.org/wiki/Adenovirus_E1B_protein.*
Fibroblast. 2015. On the web at en.wikipedia.org/wiki/Fibroblast.*
Green et al. 1965. Synthesis of collagen by mammalian cell lines of fibroblastic and nonfibroblastic origin. PNAS. 53:1360-1365.*
The International Search Report and Written Opinion from PCT/EP2012/058881, dated Aug. 27, 2012.
Database UniProt, Accession No. C3KJ33, "SubName: Full=Cell division control protein 42 homolog," Jun. 16, 2009 (1 page).
Fischer et al.; "While E1A can facilitate epithelial cell transformation by several dominant oncogenes, the C-terminus seems only to regulate rac and cdc42 function, but in both epithelial and fibroblastic cells"; *Virology;* 269:404-419 (2000).
Harris et al.; "Cdc42 and vesicle trafficking in polarized cells"; *Traffic.* 11:1272-1279 (2010).
Li et al.; "Specific contributions of the small GTPases Rho, Rac, and Cdc42 to Dbl transformation"; *J. Biol. Chem.*; 274(33):23633-23641 (1999).
Tu et al.; "Antiapoptotic Cdc42 mutants are potent activators of cellular transformation"; *Biochem.* 41:12350-12358 (2002).
Vanni et al.; "Constitutively active cdc42 mutant confers growth disadvantage in cell formation"; *Cell Cycle* 4(11):1675-1682 (2005).

* cited by examiner

*Primary Examiner* — Karen Cochrane Carlson
(74) *Attorney, Agent, or Firm* — Kilpatrick Townsend & Stockton LLP

(57) ABSTRACT

The present invention relates to a cell for producing a secreted protein comprising a polynucleotide comprising a nucleic acid sequence encoding a fast cycling cdc42 mutant and a polynucleotide comprising a nucleic acid sequence encoding a secreted protein. It also relates to a method for producing said cell and to a method for producing a secreted protein using said cell.

17 Claims, 12 Drawing Sheets

ENHANCEMENT OF PROTEIN PRODUCTION YIELD MEDIATED BY A FAST SHUTTLING CDC42 GTPASE

CROSS-REFERENCE TO RELATED APPLICATIONS

The present application is the US National Stage (371) of International Application No. PCT/EP2012/058881, filed May 14, 2012, which claims priority to U.S. Provisional Application No. 61/485,286, filed May 12, 2011, the disclosures of each are herein incorporated by reference.

REFERENCE TO A SEQUENCE LISTING SUBMITTED AS AN ASCII TEXT FILE

The Sequence Listing written in file SEQTXT_513-22_PCTUS.txt, created on Nov. 11, 2013, 16,409 bytes, machine format IBM-PC, MS-Windows operating system, is hereby incorporated by reference in its entirety for all purposes.

The present invention relates to a cell for producing a secreted protein comprising a polynucleotide comprising a nucleic acid sequence encoding a fast cycling cdc42 mutant and a polynucleotide comprising a nucleic acid sequence encoding a secreted protein. It also relates to a method for producing said cell and to a method for producing a secreted protein using said cell.

BACKGROUND OF THE INVENTION

Many of the current recombinant therapeutic proteins are complex biopharmaceuticals that require manufacturing processes based on eukaryotic cell culture technology. While prokaryotic systems are also suited to produce certain recombinant therapeutic proteins at large scale, many of the more complex biopharmaceuticals are produced in eukaryotic cells, since these cells are able to support correct folding, processing and post-translational modification.

Any increase in volumetric productivity in eukaryotic cell culture has a direct impact on costs for these complex biopharmaceuticals and is, thus, desirable both from a commercial and healthcare socioeconomic view. The yield of any biopharmaceutical production process depends on the cumulative amount of protein product which the producing cells secrete per unit time when grown under regulated process conditions.

Several avenues have been pursued to boost production yields from mammalian cell culture with great success resulting in 10-20 fold yield increase over the past decade. Mammalian cell based production systems start to match with lower prokaryotic systems in volumetric yields while they still lag behind in fermenter occupancy times. Media and fed-batch process design allowed maintaining highest viable cell densities and have contributed significantly to this success.

The producer cell itself offers potential for improvement. All steps involved in the expression and secretion of heterologous proteins such as transcription, RNA transport, translation, post-translational modification and protein transport are tightly regulated and have a strong impact on the specific productivity. This complex pattern of features also including growth properties, low sensitivity to apoptosis and specific nutrient requirements provides the basis for the selection of existing cell lines for large scale production of biopharmaceuticals. While the cell lines were selected for serum and growth factor independence as well as suspension growth using genetic and epigenetic flexibility, molecular optimization focused on transcription first.

In contrast to artificial transcription factors or polymerases that did not provide a large benefit, protection from gene inactivation is considered essential. Promoter regions from housekeeping genes equipped for continuous expression or individual elements isolated from those promoters such as ubiquitous chromatin opening elements (UCOEs) and scaffold/matrix-associated regions (S/MARs) alter the chromatin structure of promoter regions, allowing free access by the polymerase II complex thereby reducing the number of clones to be screened and causing expression stability.

Nutrient depletion, waste byproduct accumulation, extended exposure to impeller shear forces and other factors that occur during fermentation constitute apoptotic stimuli which can decrease cell viability. Therefore, anti-apoptotic genes of the bcl-2 family (Kaufmann and Fussenegger, 2003) were intensively investigated. Since the integral of viable cell density (IVCD) is one of the factors that impact the overall volumetric productivity in mammalian cell culture, it is desirable to keep cell viability at a high level over the duration of upstream processing. Production processes with cell lines that overexpressed anti-apoptotic genes showed prolonged cell culture viability and occasionally increased product yields (Chiang and Sisk, 2005).

Another bottleneck for high-yield production of heterologous proteins in eukaryotic cells is the secretory transport machinery of the producer cell line. The expression and secretion of heterologous proteins in non-polarized eukaryotic cells is a complex regulated multi-step process with multiple actuating variables. In a first step, the gene encoding the secreted protein is transcribed into mRNA which is then exported into the cytosol. mRNAs encoding proteins destined for secretion into the extracellular space or to the plasma membrane are recognized by the signal recognition particle and transported to ribosomes located on the outer membrane of the rough endoplasmic reticulum. There, the nascent proteins are co-translationally imported into the luminal space of the endoplasmic reticulum where certain sorting mechanisms apply. From there, they are packed in lipid vesicles and transported to the proximal cisternae of the Golgi apparatus and finally they are packaged into vesicles emerging from the distal trans-Golgi network (TGN) which are then transported to the plasma membrane where they are released into the culture medium. The entire secretion process is not straightforward but highly regulated on various levels. Known checkpoints and feedback loops of the secretion pathway include the Calnexin/Calreticulin System, the Unfolded protein response and ER overload response.

As a logical consequence of this complexity, the elimination of one bottleneck at early process stages is likely to lead to the creation of other bottlenecks either further downstream in the process chain or even in other crucial parallel sidelines of the secretion process. There is evidence in the literature that widening of the transcription and translation bottleneck is only effective up to a certain threshold. The specific productivity of a producer cell line has been reported to correlate linearly with the level of product gene transcription until a certain threshold mRNA-level is reached (Barnes et al., 2007). Further enhancement of transcriptional activity to mRNA levels beyond this threshold does not cause further titer increment. Rather, productivity even goes down as translation from the excess mRNA causes an overload of the protein synthesis, folding or transport machinery which in turn results in an intracellular accumulation of the protein product and concurrent triggering of the ER-Overload- and Unfolded Protein Response. As one of its consequences, the alpha subunit of the polypeptide chain initiation factor eIF2 is phosphorylated. The phosphorylated eIF2α inhibits the guanine nucleotide exchange factor eIF2β and prevents its recycling during protein synthesis. As a result, the overall rate of protein synthesis is diminished.

Specific differentiated cells such as plasma cells show very high protein secretion rates. This capacity is acquired during the terminal differentiation of B cells and has been associated with the expression of a splice form of the transcription factor XBP (Iwakoshi et al., 2003). XBP-1 regulates this differentiation process by binding to ER stress responsive elements (ERSE) within the promoters of a wide spectrum of secretory pathway genes. The XBP-1 mediated differentiation process results in a physical expansion of the ER, increased mitochondrial mass and function, larger cell size and enhanced total protein synthesis (Shaffer et al., 2004). This complex functional change is associated with cell cycle arrest.

Almost all cell types involved in high-level protein secretion (pancreatic beta cells, leydig cells, glandular cells, etc.) are terminally differentiated, are not able to proliferate and have a limited life-span before ultimately undergoing programmed cell death (Chen-Kiang, 2003). Unsurprisingly, attempts to increase protein secretion by overexpressing XBP-1 in non-plasma cells, especially production cell lines such as CHO-K1 cells, were only successful in increasing protein secretion to a limited extent (Tigges and Fussenegger, 2006). A high proliferation rate during early process phases and high cell viability remain critical for modern fed-batch production processes.

This general paradigm holds true for other factors upstream of XBP-1 capable of enhancing the secretory capacity such as ATF6 and IRE1α. Higher cell specific productivity due to enhanced secretion needs to compensate for lower viable cell mass and shorter process duration before higher yields are feasible. Moreover, expression of growth inhibitory genes is difficult to maintain and process robustness may suffer.

Molecular chaperones such as binding protein BiP/GRP78 and protein disulfide isomerase (PDI) are downstream effectors of XPB. BiP associates with the antibody heavy chain before its displacement by the light chain and plays a major role in its folding. Both BiP/GRP78 and protein disulfide isomerase (PDI) have been considered for secretion enhancement but were not yet successful in improving upstream yield. In contrast to what could be expected, BiP overexpression in mammalian cells has been shown to reduce rather than to increase the secretion of proteins with which BiP associates with (Domer and Kaufman, 1994). Likewise, PDI overexpression in CHO cells reduced the expression of a TNFR:FC fusion protein (Davis et al., 2000), whereas the specific production rate of an antibody could be increased by 40% (Borth et al., 2005).

Thus, there are different bottlenecks within the protein secretion machinery which are not yet overcome.

Further, the fact that an increase of the protein folding capacity of a cell creates a protein production bottle neck further downstream, is supported by a report describing ER to cis-Golgi transport problems for IFN-gamma production in a CHO cell line (Hooker et al., 1999). Other additional bottlenecks are expected further downstream in the cellular secretion machinery.

All of the above-described examples show that multiple bottlenecks, for example, within the protein production machinery and/or protein secretion machinery, exist which have to be overcome in order to optimize the preparation of secreted proteins in cells.

Thus, there is a need for protein producing cells comprising a regulator protein having an effect on multiple levels of cellular function. Said effect on multiple levels of cellular function should result in an enhancement of protein production and/or protein secretion, particularly in large-scale industrial protein production processes, e.g. industrial fed batch processes. There is also a need for a method for producing proteins (e.g. therapeutic proteins) using said cells.

Systems biology approaches, in particular comparative transcriptome and proteome analysis of high and low expressing cells, may identify molecular targets that help to overcome productivity bottlenecks. However, the combined expression of multiple regulators in a well adjusted and stable fashion is rather complex and may not be practical in all cases. On the other hand, the expression of individual high level regulators is an approach that allows to affect multiple pathways simultaneously. Nevertheless, the pleiotropic effects of such active high level regulator proteins and their mutants makes it difficult to predict how their expression within the cellular context will affect upstream product yield in industrial fed batch processes.

Many approaches for yield-enhancement by cell line engineering have focused on single enzymes and regulator proteins in the past. Only few attempts have been made to investigate the potential of regulator proteins that are known for their pleiotropic effects on multiple levels of cellular function. To some extent, the lack of research in this field may have resulted from the contradictive findings as reported in the literature and as described above.

One protein family that contains known high level regulators with pleiotropic effector functions is the GTPase superfamily.

The superfamily of small GTP binding proteins contains more than 100 members that can be divided into five groups, namely into the Ras, Rho, Rab, Sar/Arf and Ran group, based on structural and functional differences. Whereas regulation of gene expression has initially been associated only with the Ras proteins and vesicular transport with the Sar/Arf proteins, the Rho proteins were thought to control the organization of the cytoskeleton (Takai et al., 2001). It has later been shown that besides actin organization the three major members of the Rho family, namely Rho, cdc42 and Rac, are involved in processes of cell cycle progression, transcription, cell-cell adhesion, cell motility, vesicle shuttling, secretion, endocytosis, phagocytosis, mitogenesis, and/or apoptosis. This pleiotropic activity makes the Rho GTPases to interesting candidates as general regulators of cellular processes. However, only part of the natural responses will have the technically desired direction. For example, cell cycle promotion may induce proapoptotic signals, while differentiation may lead to ER expansion and enhanced secretory capacity.

Rho GTPases exist in an inactive GDP-bound and an active GTP-bound form. In their active conformation they can interact with a large number of effectors regulating multiple signal transduction pathways. Activation of Rho GTPases is mediated by guanine nucleotide exchange factors (GEFs) which catalyze the replacement of GDP by GTP. Only a fraction of the more than 80 GEFs known to date have been characterized in detail, but it is clear that many GEFs can activate more than one Rho GTPase (Schmidt and Hall, 2002). The activity of the Rho proteins, including cdc42, depends on their GTPase cycle. Said proteins are active in their GTP-bound form and inactive in their GDP-bound form. Three types of regulatory proteins control said GTPase cycle: (i) the Guanine nucleotide exchange factors (GEFs), (ii) the GTPase activating proteins (GAPs), and (iii) the Guanine nucleotide dissociation inhibitors (GDIs). The complexity of the functional network of Rho GTPases may provide an explanation for the seemingly contradictive effects of Rho GTPase overexpression that has been reported in the literature.

The GEF proteins that control Rho GTPases are tightly regulated themselves by inhibitory domains or inhibitor proteins and are activated upon dephosphorylation. Members of the dbl family of oncogenes that are overexpressed in a variety of cancer types represent guanine nucleotide exchange factors (GEFs) for cdc42 that help to maintain cdc42 in its activated state. This may led to the assumption that permanently active (GTP-bound) cdc42 could activate cell growth, and other functions attributed to cdc42. While heterologous overexpression of a tightly regulated protein is expected to have little functional impact, overexpression of a permanently activated regulator protein maintained in its activated state would be desirable. For cdc42, the permanently active mutants cdc42Q61L and cdc42V12 have been isolated. These mutants were shown to have positive effects on total secretion rates of p75, while LDLR secretion was inhibited in MDCK cells (Müsch et al., EMBO J. 2001 May 1; 20(9): 2171-2179). Efficient movement of correctly folded proteins from the ER to the Golgi is considered as an essential step in the production of secreted proteins. Contrary to expectations, it was found that expression of a permanently active GTPase-defective Cdc42 mutant led to growth inhibition or apoptosis. Moreover, the same constitutively active mutant cdc42Q61L was shown to block the ER to Golgi transport of VSVG (Wu 2000 Nature).

To resolve the scientifically contradictory results and to obtain cdc42s which are more active than the natural cdc42s, fast cycling cdc42 mutants such as cdc42F28L (R. Lin et al., A novel Cdc42Hs mutant induces cellular transformation. Curr. Biol. 7 (1997), pp. 794-797) or cdc42D118N (S. Tu et al., Antiapoptotic Cdc42 mutants are potent activators of cellular transformation. Biochemistry 41 (2002), pp. 12350-12358) have been generated. These mutants can undergo spontaneous GTP-GDP exchange while maintaining full GTPase activity. These mutants are no longer dependent on induction by dbl. Said mutants are self-activating mutants. The fast cycling cdc42 mutants such as cdc42F28L do not block trafficking as the permanently active cdc42 mutants (Wu 2000 Nature), but cause moderate acceleration. The cdc42F28L mutant, for example, survived in NIH 3T3 fibroblasts and allowed anchorage independent growth and increased growth rates in media with reduced serum (Tu et al., 2002). However, increased growth rates may contradict a high productivity as it is generally accepted that fast replication does not allow to build up the membrane systems required for efficient secretion and folding.

Cdc42 appears as one of the very broad and heterogeneous regulators of cellular activity. Nevertheless, as discussed above, the natural, permanently active and inactive forms of cdc42 have demonstrated features incompatible with a production cell. So far, cdc42 mediated active actin reorganization, fast cycling of vesicles and/or induction of anchorage independence has/have not been linked with increased productivity of non-adherent cells.

In a screen under industrial protein production process relevant conditions, the inventors of the present invention surprisingly found that fast cycling cdc42 mutants exert a net beneficial effect on protein yields obtained in non-adherent cell cultures. Said fast cycling cdc42 mutants directly boost productivity of non-adherent cell cultures, e.g. in a bioreactor setting. In particular, the fast cycling cdc42 mutants accelerate trafficking of proteins from the ER to the Golgi. As mentioned above, efficient movement of correctly folded proteins from the ER to the Golgi is considered as an essential step in the production of secreted proteins.

The inventors of the present invention further found that the beneficial effect of the fast cycling cdc42 mutants on protein yields is independent of the order in which the heterologous genes are introduced into the non-adherent cells. For example, said effect is achieved when (i) a high producer cell clone expressing the protein of interest is subsequently transfected with a nucleic acid sequence encoding a fast cycling cdc42 mutant, (ii) a naïve non-adherent cell is modified with a fast cycling cdc42 mutant to create a superior starter cell that is subsequently transfected with a nucleic acid sequence encoding the protein of interest or (iii) a naïve non-adherent cell is transfected simultaneously with a nucleic acid sequence encoding a fast cycling cdc42 mutant and with a nucleic acid sequence encoding the protein of interest.

SUMMARY OF THE INVENTION

In a first aspect, the present invention relates to a non-adherent cell for producing a secreted protein comprising
(i) a polynucleotide comprising a nucleic acid sequence encoding a fast cycling cdc42 mutant, and
(ii) a polynucleotide comprising a nucleic acid sequence encoding a secreted protein.

In a second aspect, the present invention relates to a method for preparing a non-adherent cell according to the first aspect comprising the following steps:
(i) providing a non-adherent cell or an adherent cell,
(ii) transfecting said cell with a polynucleotide comprising a nucleic acid sequence encoding a fast cycling cdc42 mutant, and
(iii) transfecting said cell with a polynucleotide comprising a nucleic acid sequence encoding a secreted protein,
wherein the adherent cell provided in step (i) is transferred into a non-adherent state after performance of step (ii) or (iii), and
wherein optionally, the cell of step (ii) or the cell of step (iii) is further transfected with a polynucleotide comprising an E1B gene region.

In a third aspect, the present inventions relates to a method for producing a secreted protein comprising the following steps:
(i) providing a non-adherent cell according to the first aspect,
(ii) culturing said cell, and
(iii) harvesting the secreted protein produced by said cell.

This summary of the invention does not necessarily describe all features of the invention.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety. Nothing herein is to be construed as an admission that the invention is not entitled to antedate such disclosure by virtue of prior invention.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. As used in this specification and the appended claims, the singular forms "a", "an", and "the" include plural referents, unless the content clearly dictates otherwise.

Cell line engineering is one of the major avenues that are being pursued to achieve an increase of the cumulative amount of protein product that the producing cells secrete per unit time when grown in industrial protein production processes.

Many approaches for yield-enhancement by cell line engineering have focused on single enzymes and regulator proteins in the past. Only few attempts have been made to investigate the potential of regulator proteins that are known for their pleiotropic effects on multiple levels of cellular function. To some extent, the lack of research in this field may have resulted from the contradictive findings as reported in the literature.

As mentioned above, the inventors of the present invention surprisingly found that the expression of a fast cycling cdc42 mutant has a beneficial effect on the yield of a protein produced in non-adherent cells. In particular, the fast cycling cdc42 mutant accelerates trafficking of proteins from the ER to the Golgi. As mentioned above, efficient movement of correctly folded proteins from the ER to the Golgi is considered as an essential step in the production of secreted proteins.

Thus, in a first aspect, the present invention relates to a non-adherent cell for producing a secreted protein comprising
(i) a polynucleotide comprising, essentially consisting of, or consisting of a nucleic acid sequence encoding a fast cycling cdc42 mutant, and
(ii) a polynucleotide comprising, essentially consisting of, or consisting of a nucleic acid sequence encoding a secreted protein.

The term "cdc42 protein", as used herein, refers to a protein which belongs to the superfamily of small GTP binding. Said superfamily contains a variety of members that can be divided into the subfamilies Ras, Rho, Rab, Sar/Arf and Ran based on structural and functional differences. The cdc42 protein is a small GTPase of the Rho-subfamily. The cdc42 protein exists in an inactive GDP-bound and active GTP-bound form. In its active configuration, it can interact with a large number of effectors regulating multiple signal transduction pathways. The cdc42 protein is, for example, involved in processes of actin organization, cell cycle progression, transcription, cell-cell adhesion, cell motility, vesicle shuttling, secretion, endocytosis, phagocytosis, mitogenesis, and/or apoptosis. Activation of the cdc42 protein is mediated by Guanine nucleotide exchange factors (GEFs), particularly by dbl proteins, which catalyze the replacement of GDP by GTP. Other members of the Rho family are the proteins Rho and Rac proteins (see also introductory part of the description).

The term "fast cycling cdc42 mutant", as used herein, refers to a protein which differs in comparison to the cdc42 protein from which it is derived by one or more change(s) (mutation(s)) in the amino acid sequence. The cdc42 protein from which the cdc42 mutant is derived is also designated as wild-type cdc42 protein. The wild-type cdc42 protein has the amino acid sequence according to SEQ ID NO: 8. The one or more change(s), e.g. 1, 2, 3, 4, 5, 6, 7, 8, 9, or 10 change(s), in the amino acid sequence may be one or more amino acid substitution(s), insertion(s), deletion(s), addition(s), N-terminal truncations, or C-terminal truncations, or any combination of these changes. Said one or more change(s) in the amino acid sequence is (are) such that it (they) allow(s) the cdc42 mutant to change between its GDP-bound inactive form and GTP-bound active form independently from the presence of Guanidine nucleotide exchange factors (GEFs). This means that the "fast cycling cdc42 mutant" can bind GTP in the absence of Guanidine nucleotide exchange factors (GEFs). It is, therefore, self-activating. In other words, said one or more change(s) in the amino acid sequence of cdc42 mimic(s) the functional activity of Guanidine nucleotide exchange factors (GEFs), particularly of dbl proteins, and cause the constitutive exchange of GDP for GTP. This behavior is known as "fast cycling" or "fast shuttling". Because of the ability of the above described "fast cycling cdc42 mutant" for self-activation, it is also designated as an actively shuttling variant of the cdc42 protein.

In addition to the above described one or more amino acid change(s) which allow the "fast cycling" of the cdc42 mutant, said mutant may comprise one or more further amino acid change(s), e.g. 1, 2, 3, 4, 5, 6, 7, 8, 9, or 10 change(s), such as amino acid substitution(s), insertion(s), deletion(s) and/or addition(s) compared to the respective wild-type cdc42 amino acid sequence, provided that said amino acid change(s) do not negatively influence the ability of the cdc42 mutant for "fast cycling".

The term "fast cycling cdc42 mutant", as used herein, encompasses fast cycling cdc42 mutants in any species, e.g. in humans or rodents such as mice or rats. The fast cycling cdc42 mutant may be a non-naturally occurring mutant, for example, a mutant constructed artificially, e.g. by gene-technological means, or a naturally occurring mutant. Naturally occurring fast cycling cdc42 mutants may be homologs, orthologs, or paralogs in the same or in a different species, in particular in humans or rodents such as mice or rats.

The person skilled in the art can easily assess whether a cdc42 mutant has the ability for "fast cycling". As described herein (see, for example, exemplary part), cells comprising a fast cycling cdc42 mutant display higher specific productivities compared to cells which do not comprise a fast cycling cdc42 mutant. In addition, it is clear that cells comprising a fast cycling cdc42 mutant display higher specific productivities compared to cells which comprise a cdc42 mutant not having the ability for fast cycling.

The term "productivity", as used herein, describes the ability of cells to synthesize and release a defined amount of a secreted protein (i.e. the protein of interest) (titer), particularly under defined culturing conditions. In the context of industrial manufacturing, the productivity is usually expressed as amount of protein in picogram (pg) produced.

The term "specific productivity", as used herein, describes the ability of a defined number of cells to synthesize and release a defined amount of a secreted protein (i.e. the protein of interest) that leaves the cells and accumulates in the culture medium within a defined time, e.g. 24 hours or multiple days such as 2, 3, 4, or 5 days, particularly under defined culturing conditions. The specific productivity is, therefore, a quantitative measure for the capacity of cells to express/synthesize/produce a secreted protein (i.e. the protein of interest). In the context of industrial manufacturing, the specific productivity is usually expressed as amount of protein in picogram produced per cell and day ('pg/cell*day' or 'pcd').

One method to determine the "(specific) productivity" of a secreted protein (i.e. the protein of interest) is, for example, to quantitatively measure the amount of protein which is secreted into the culture medium with an enzyme linked immunosorbent assay (ELISA). For this purpose, cells are seeded into fresh culture medium at defined densities. After a defined time, e.g. after 24 hours or multiple days such as 2, 3, 4, or 5 days, particularly under defined culturing conditions, a sample from the cell culture medium, preferably a sample from the cell supernatant, is taken and subjected to ELISA measurement to determine the titer of the secreted protein (i.e. the protein of interest). The specific productivity can be determined by dividing the titer by the average cell number and the time.

The term "enhanced or increased specific productivity", as used herein, describes the ability of a defined number of modified cells according to the invention, e.g. cells comprising a fast cycling cdc42 mutant or cells comprising a fast cycling cdc42 mutant and proteins encoded by the E1B gene region, such as E1B 19K and E1B 55K, to synthesize and release higher amounts of a secreted protein (i.e. the protein of interest) within a defined time, e.g. 24 hours or multiple days such as 2, 3, 4, or 5 days, compared to unmodified control cells, e.g. cells not comprising a fast cycling cdc42 mutant or cells not comprising a fast cycling cdc42 mutant and proteins encoded by the E1B region, such as E1B 19K and E1B 55K.

The term "enhanced or increased specific productivity", as used herein, also describes the ability of a defined number of modified cells according to the invention, e.g. cells comprising a fast cycling cdc42 mutant or cells comprising a fast cycling cdc42 mutant and proteins encoded by the E1B gene region, such as E1B 19K and E1B 55K, to synthesize and release higher amounts of a secreted protein (i.e. the protein of interest) within a defined time, e.g. 24 hours or multiple days such as 2, 3, 4, or 5 days, compared to cells comprising a cdc42 mutant which has not the ability for fast cycling.

The differences between the determined values have to be statistically significant. Statistically significant data may be achieved, for example, by carrying out a t-test or limma test. In preferred embodiments, the difference is sufficient, if the (specific) productivity is increased by at least 20% or 30%, more preferably by at least 40% or 50% and most preferably by at least 50% or 100%, e.g. by at least 20, 30, 40, 50, 60, 70, 80, 90, or 100%, in the modified cells as defined above compared to the control cells as defined above. The cells under investigation can be heterogeneous populations or clonal cell lines of modified cells. Non-treated, non-transfected or non-modified cells can serve as control cells.

When referring to a secreted protein (i.e. the protein of interest), the terms "enhanced/increased/improved productivity" and "enhanced/increase/improved yield" have the same meaning and are used interchangeably herein.

Thus, to determine whether a cdc42 mutant has the ability for fast cycling, the skilled person may culture under comparable conditions, for example, (i) cells comprising a potentially fast cycling cdc42 mutant and a secreted protein and (ii) cells comprising no fast cycling cdc42 mutant (negative control). As a positive control, (iii) cells comprising a cdc42 mutant which is known to fast cycle may additionally or alternatively be cultured. The skilled person may determine the (specific) productivity as defined above and may compare the different values with each other. If the cells comprising the potentially fast cycling cdc42 mutant display higher (specific) productivities compared to cells which do not comprise a cdc42 mutant and/or display comparable (specific) productivities compared to cells which comprise a cdc42 mutant known to fast cycle, the cdc42 mutant tested may be considered as a cdc42 mutant which has the ability for fast cycling. As mentioned above, the differences between said values have to be statistically significant. In preferred embodiments, the cells comprising a cdc42 mutant which is able for fast cycling display a (specific) productivity which is increased by at least 20% or 30%, more preferably by at least 40% or 50% and most preferably by at least 50% or 100% compared to cells which do not comprise a cdc42 mutant.

In this respect, it should be noted that the mutants cdc42Q61L and cdc42V12 are not encompassed by the term "fast cycling" cdc42 mutants. Said mutants are permanently active mutants. They are not able to shuttle between the GDP and GTP state.

Preferably, (i) the fast cycling cdc42 mutant is expressed from a polynucleotide stably maintained in said cell (e.g. either episomally or chromosomally), and (ii) the secreted protein is expressed from a polynucleotide transiently present in said cell or stably maintained in said cell (e.g. either episomally or chromosomally).

The polynucleotide comprising the nucleic acid sequence encoding the fast cycling cdc42 mutant and polynucleotide comprising the nucleic acid sequence encoding the secreted protein may be integrated into one expression vector or into separate expression vectors which is (are) used to transfect the cell. Suitable expression vectors comprise plasmids, cosmids, bacterial artificial chromosomes (BAC) and viral vectors. Preferably, non-viral expression vectors are used.

The expression of the nucleic acid sequence encoding the fast cycling cdc42 mutant and/or the nucleic acid sequence encoding the secreted protein may be controlled by expression control sequences. The term "expression control sequences" refers to nucleotide sequences which affect the expression of coding sequences to which they are operably linked in a cell (e.g. an eukaryotic cell). Expression control sequences are sequences which control the transcription, e.g. promoters or enhancers, post-transcriptional events, e.g. polyadenylation, and the translation of nucleic acid sequences.

It is preferred that the nucleic acid sequence encoding the fast cycling cdc42 mutant and/or the nucleic acid sequence encoding the secreted protein is (are) under control of a constitutive promoter, preferably under control of a human translocation elongation factor 2 (EF2) promoter. Other constitutive promoters are well known in the art.

The above mentioned polynucleotides may comprise nucleic acid sequences encoding tags. In preferred embodiments, tags are used which allow the detection of the fast cycling cdc42 mutant or which allow the detection, harvest and/or purification of the secreted protein.

Preferably, the nucleic acid sequence encoding the tag is operably linked to the nucleic acid sequence encoding the fast cycling cdc42 mutant and/or secreted protein to be tagged. Preferably, the tag is a fluorescent tag such as GFP or EGFP. A FLAG tag is also preferred, e.g. a FLAG tag which is located at the N-terminus or C-terminus of the expressed secreted protein. A FLAG tag can be used to purify the secreted protein, for example, from the cell supernatant, e.g. with affinity chromatography. It can also be used to harvest/isolate the secreted protein from the culture medium. In addition, a FLAG-tag can be used in many different assays that require recognition by an antibody. If there is no antibody against the protein, adding a FLAG-tag to this protein allows one to follow the protein with an antibody against the FLAG sequence. Examples are cellular localization studies by immunofluorescence or detection by SDS-PAGE protein electrophoresis.

The term "operably linked" means that a nucleic acid sequence is linked to another nucleic acid in such a way that in-frame expression of a corresponding construct can be affected avoiding frame-shifts or stop codons. Particularly, the term means the linking of expression control sequences to a coding nucleic acid sequence of interest to effectively control the expression of said sequence (see above) or the term means the linking of nucleic acid sequences encoding a tag to a coding nucleic acid sequence of interest (see above).

It is preferred that the fast cycling cdc42 mutant is stably expressed from a polynucleotide stably maintained in said cell or that the fast cycling cdc42 mutant and the secreted protein are stably expressed from polynucleotides stably maintained in said cell.

The term "stable expression" as used herein refers to a constantly maintained transcription and/or translation of the nucleic acid sequence encoding the fast cycling cdc42 mutant or the secreted protein within the cell. The level of expression in a cell may be determined on the basis of either the amount of corresponding mRNA that is present in the cell or the amount of the protein/mutant produced by said cell (see examples). mRNA transcribed from a nucleic acid sequence can be quantified by various assays, e.g. by Northern blot hybridization, ribonuclease RNA protection, in situ hybridization to cellular RNA or by PCR. In addition or alternatively, proteins encoded by a nucleic acid sequence can also be quantified by various methods, e.g. ELISA, by assaying for the biological activity of the protein, by immunostaining of the protein followed by FACS analysis or by homogeneous time-resolved fluorescence (HTRF) assays. Preferably, "stable expression" means that such constructs are not subject to inactivation by silencing events such as methylation. Particularly, for long-term, high-yield production of the secreted protein, stable expression is preferred.

Preferably, the fast cycling cdc42 mutant and/or the secreted protein (i.e. the protein of interest) is (are) exogenous protein(s). The term "exogenous protein" means any protein that is expressed inside the cell from a polynucleotide introduced into the cell. Preferably, the fast cycling cdc42 mutant and/or the secreted protein (i.e. the protein of interest) is (are) recombinantly expressed in the cell. Alternatively, the term "heterologous protein" (e.g. heterologous fast cycling cdc42 mutant or heterologous secreted protein) may be used.

In contrast thereto, the term "endogenous protein" is usually used to refer to a protein that is naturally encoded by the genome of the cell.

It is further preferred that the nucleic acid sequence encodes
(i) a fast cycling cdc42 mutant with an amino acid sequence, wherein the amino acid F at amino acid position 28 (of the wild-type cdc42 amino acid sequence) or at an amino acid position corresponding thereto is replaced by a non-polar amino acid, preferably by L,
(ii) a fast cycling cdc42 mutant with an amino acid sequence, wherein the amino acid D at amino acid position 118 (of the wild-type cdc42 amino acid sequence) or at an amino acid position corresponding thereto is replaced by a polar amino acid, preferably by N, or
(iii) a fast cycling cdc42 mutant with an amino acid sequence, wherein the amino acid F at amino acid position 28 (of the wild-type cdc42 amino acid sequence) or at an amino acid position corresponding thereto is replaced by a non-polar amino acid, preferably by L, and the amino acid D at amino acid position 121 (of the wild-type cdc42 amino acid sequence) or at an amino acid position corresponding thereto is replaced by a polar amino acid, preferably by N.

The terms "polypeptide" and "protein" are used interchangeably herein and mean any peptide-linked chain of amino acids, regardless of length or post-translational modification. A protein may contain more than one polypeptide chain.

In the context of the present invention, residues in two or more polypeptides are said to "correspond" to each other if the residues occupy an analogous position in the polypeptide structures. As is well known in the art, analogous positions in two or more polypeptides can be determined by aligning the polypeptide sequences based on amino acid sequence or structural similarities. Such alignment tools are well known to the person skilled in the art and can be, for example, obtained on the World Wide Web, e.g., ClustalW (www.ebi.ac.uk/clustalw) or Align (http://www.ebi.ac.uk/emboss/align/index.html) using standard settings, preferably for Align EMBOSS::needle, Matrix: Blosum62, Gap Open 10.0, Gap Extend 0.5. Those skilled in the art understand that it may be necessary to introduce gaps in either sequence to produce a satisfactory alignment. Residues in two or more Serpin A1 iso forms are said to "correspond" if the residues are aligned in the best sequence alignment. The "best sequence alignment" between two polypeptides is defined as the alignment that produces the largest number of aligned identical residues. The "region of best sequence alignment" ends and, thus, determines the metes and bounds of the length of the comparison sequence for the purpose of the determination of the similarity score, if the sequence similarity, preferably identity, between two aligned sequences drops to less than 30%, preferably less than 20%, more preferably less than 10% over a length of 10, 20 or 30 amino acids.

It is preferred that the non-polar amino acid is selected from the group consisting of G, A, V, L, I, M, W, or P and/or the polar amino acid is selected from the group consisting of S, T, C, Y, N, or Q. It is particularly preferred that (i) the non-polar amino acid is G and the polar amino acid is selected from the group consisting of S, T, C, Y, N, or Q, (ii) the non-polar amino acid is A and the polar amino acid is selected from the group consisting of S, T, C, Y, N, or Q, (iii) the non-polar amino acid is V and the polar amino acid is selected from the group consisting of S, T, C, Y, N, or Q, (iv) the non-polar amino acid is L and the polar amino acid is selected from the group consisting of S, T, C, Y, N, or Q, (v) the non-polar amino acid is I and the polar amino acid is selected from the group consisting of S, T, C, Y, N, or Q, (vi) the non-polar amino acid is M and the polar amino acid is selected from the group consisting of S, T, C, Y, N, or Q, (vii)

the non-polar amino acid is W and the polar amino acid is selected from the group consisting of S, T, C, Y, N, or Q, or (viii) the non-polar amino acid is P and the polar amino acid is selected from the group consisting of S, T, C, Y, N, or Q.

It is also particularly preferred that (i) the polar amino acid is S and the non-polar amino acid is selected from the group consisting of G, A, V, L, I, M, W, or P, (ii) the polar amino acid is T and the non-polar amino acid is selected from the group consisting of G, A, V, L, I, M, W, or P, (iii) the polar amino acid is C and the non-polar amino acid is selected from the group consisting of G, A, V, L, I, M, W, or P, (iv) the polar amino acid is Y and the non-polar amino acid is selected from the group consisting of G, A, V, L, I, M, W, or P, (v) the polar amino acid is N and the non-polar amino acid is selected from the group consisting of G, A, V, L, I, M, W, or P, or (vi) the polar amino acid is Q and the non-polar amino acid is selected from the group consisting of G, A, V, L, I, M, W, or P.

It is more preferred that the nucleic acid sequence encodes a cdc42F28L mutant, a cdc42D118N mutant, or a cdc42F28L/D121N mutant. It is particularly more preferred that the nucleic acid sequence encodes a cdc42F28L mutant.

It is most preferred that the nucleic acid sequence encodes
(i) a cdc42F28L mutant with an amino acid sequence according to SEQ ID NO: 1 or a variant thereof which is at least 90%, more preferably at least 95%, most preferably at least 99%, e.g. 90, 91, 92, 93, 94, 95, 96, 97, 98, or 99%, identical to said amino acid sequence,
(ii) a cdc42D118N mutant with an amino acid sequence according to SEQ ID NO: 5 or a variant thereof which is at least 90%, more preferably at least 95%, most preferably at least 99%, e.g. 90, 91, 92, 93, 94, 95, 96, 97, 98, or 99%, identical to said amino acid sequence, or
(iii) a cdc42F28L/D121N mutant with an amino acid sequence according to SEQ ID NO: 6 or a variant thereof which is at least 90%, more preferably at least 95%, most preferably at least 99%, e.g. 90, 91, 92, 93, 94, 95, 96, 97, 98, or 99%, identical to said amino acid sequence.

It is particularly most preferred that the nucleic acid sequence encodes a cdc42F28L mutant with an amino acid sequence according to SEQ ID NO: 1 or a variant thereof which is at least 90%, more preferably at least 95%, most preferably at least 99%, e.g. 90, 91, 92, 93, 94, 95, 96, 97, 98, or 99%, identical to said amino acid sequence.

It is also most preferred that the nucleic acid sequence encodes a mutant with an amino acid sequence corresponding to the amino acid sequence according to SEQ ID NO: 1 or a variant thereof, SEQ ID NO: 5 or a variant thereof, or SEQ ID NO: 6 or a variant thereof, wherein the variant in each case is at least 90%, more preferably at least 95%, most preferably at least 99%, e.g. 90, 91, 92, 93, 94, 95, 96, 97, 98, or 99%, identical to said amino acid sequence.

In preferred embodiments, the sequence identity is over a continuous stretch of at least 20, 25, 30, 35, 40, 50, 60, 70, 80, 90, 100, 120, 150, 180, 200, or more amino acids, preferably over the whole length of the respective reference polypeptide (e.g. SEQ ID NO: 1, SEQ ID NO: 5, or SEQ ID NO: 6, see above). In particularly preferred embodiments, the sequence identity is at least 95% over the whole length, is at least 96% over the whole length, is at least 97% over the whole length, is at least 98% over the whole length, or is at least 99% over the whole length of the respective reference polypeptide (e.g. SEQ ID NO: 1, SEQ ID NO: 5, or SEQ ID NO: 6, see above).

Preferably, the afore-mentioned variation(s) lies (lie) outside of the amino acid region(s) or differ(s) from the amino acid position(s) allowing "fast cycling" of the cdc42 mutant. Accordingly, it is preferred that the above-described variants still comprise (i) the amino acid L instead of F at an amino acid position 28 according to SEQ ID NO: 1 or at an amino acid position corresponding thereto,
(ii) the amino acid N instead of D at an amino acid position 118 according to SEQ ID NO: 5 or at an amino acid position corresponding thereto, or
(iii) the amino acid L instead of F at an amino acid position 28 according to SEQ ID NO: 6 or at an amino acid position corresponding thereto and the amino acid N instead of D at an amino acid position 121 according to SEQ ID NO: 6 or at an amino acid position corresponding thereto.

It is particularly preferred that the above-mentioned variants are functionally active variants. This means that the variation(s) in the amino acid sequence, preferably lying outside of the amino acid region(s) or being apart from the amino acid position(s) allowing "fast cycling", do not negatively influence the ability of the cdc42 mutant for "fast cycling".

The person skilled in the art can easily assess whether a cdc42 variant has still the ability for "fast cycling". Cells comprising a cdc42 variant which has still the ability for "fast cycling" display higher specific productivities when producing a secreted protein (i.e. the protein of interest) compared to cells which do not comprise a fast cycling cdc42 mutant or which comprise a fast cycling mutant not having the ability for "fast cycling" anymore. An exemplarily method to determine the "specific productivity" of a secreted protein (i.e. the protein of interest) is described above.

Alternatively, the variants may differs from the respective reference polypeptide (e.g. SEQ ID NO: 1, SEQ ID NO: 5, or SEQ ID NO: 6, see above) from which they are derived by one or more, e.g. 1, 2, 3, 4, 5, 6, 7, 8, 9, 10, 11, 12, 13, 14, 15, 16, 17, 18, 19, or 20, amino acid substitutions, deletions, additions, and/or insertions. Said variants are preferably functionally active variants (see above).

The variations allowed may be experimentally determined by systematically making substitutions, deletions, additions, and/or insertions of amino acids in the protein, e.g. using recombinant DNA techniques, and assaying the resulting variants, e.g. recombinant variants, for activity as described above. This does not require more than routine experiments for the person skilled in the art.

In preferred embodiments, the nucleic acid sequence encoding the cdc42 mutant, preferably the cdc42F28L mutant, and/or the nucleic acid sequence encoding the secreted protein (i.e. the protein of interest) is (are) codon optimized for expression in the cell. The term "codon optimized", as used in the context of the present invention, means, for example, the removal of internal TATA boxes, chi sites, ribosome entry sites, RNA instability motifs, repeat sequences, intense RNA secondary structures and cryptic splice sites as well as the use of codons of higher utilization in cells (e.g. eukaryotic cells) or for highly expressed genes in cells (e.g. eukaryotic cells). In more preferred embodiments, the cdc42F28L mutant is encoded by a nucleic acid sequence according to SEQ ID NO: 2. Said nucleic acid sequence is a codon-optimized sequence.

Preferably, the cell further comprises a polynucleotide comprising a nucleic acid sequence encoding the proteins E1B 19K and E1B 55K. Said E1B proteins have anti-apoptotic properties. Since the integral of viable cell density (IVCD) is one of the factors that impact the overall volumetric productivity in cell culture, it is desirable to keep cell viability at a high level over the duration of upstream processing. The inventors of the present invention surprisingly found that the overexpression of the E1B anti-apoptotic genes showed prolonged cell culture viability and occasionally increased product yields (see examples).

More preferably, the cell further comprises a polynucleotide comprising an E1B gene region. Preferably, the E1B gene region is of an Adenovirus from the genus *Mastadenovirus* (e.g. *Mastadenovirus* group C), more preferably from Adenovirus 5. It is preferred that the E1B gene region encodes the proteins E1B 19K and E1B 55K. In preferred embodiments, the E1B gene region has a nucleic acid sequence according to SEQ ID NO: 7.

The E1B 19K protein, as mentioned above, is preferably a protein with an amino acid sequence according to SEQ ID NO: 3 and the E1B 55K protein, as mentioned above, is preferably a protein with an amino acid sequence according to SEQ ID NO: 4.

Generally, cells can be grown in suspension or adherent cultures. Some cells naturally live in suspension, without being attached to a surface, such as cells that exist in the bloodstream (e.g. hematopoietic cells). Adherent cells (e.g. primary cells) require a surface, such as tissue culture plastic carrier or micro-carrier, which may be coated with extracellular matrix components to increase adhesion properties and provide other signals needed for growth and differentiation. Most cells derived from solid tissues are adherent. Adherent cells are usually used in their original form for cell biology research. There are also cells that have been modified to be able to survive in suspension cultures so that they can be grown to a higher density than adherent conditions would allow. Under adherent conditions, growth is namely limited by surface area, which may limit product yields. Such suspension adapted cells or cells adapted to non-adherent grow are usually used for bulk protein production or batch harvesting. Under non-adherent conditions, growth is limited by concentration of cells in the culture medium, which allows easier scale-up.

The cell according to the first aspect of the invention is a non-adherent cell. The term "non-adherent cell", as used herein, refers to a cell that is able to survive in a suspension culture without being attached to a surface (e.g. tissue culture plastic carrier or micro-carrier). Said cell may be a cell which can naturally live in suspension without being attached to a surface. Said cell may also be a cell which has been modified or adapted to be able to survive in a suspension culture without being attached to a surface (e.g. tissue culture plastic carrier or micro-carrier). As mentioned above, most cells are in their original, non-modified or non-adapted form, adherent cells. A non-adherent cell can usually be grown to a higher density than adherent conditions would allow. It is, thus, more suited for culturing in an industrial scale, e.g. in a bioreactor setting or in an agitated culture, for example, in order to produce proteins such as therapeutical proteins, e.g. antibodies or hormones. To make cells attractive for the production of proteins, the cells have to be adapted to a non-adherent cell culture. Because the original cells would undergo apoptosis under serum-free conditions and/or in the absence of a suitable surface, this adaptation is a prolonged process requiring passaging with diminishing amounts of serum (e.g. dilution rows from 10% to 0% Fetal Calve Serum (FCS)), thereby selecting an irreversibly modified cell population. Adapted non-adherent cells are known in the art. The skilled person is aware of protocols for transferring a cell from an adherent state into a non-adherent state (see, for example, Appl Microbiol Biotechnol. 2008 March; 78(3):391-9. Epub 2008 Jan. 9).

In contrast thereto, the term "adherent cell", as used herein, refer to a cell which requires a surface, such as tissue culture plastic carrier or micro-carrier. Said surface may be coated with extracellular matrix components to increase adhesion properties and provide other signals needed for growth and differentiation. Said cells require periodic passaging, but allow easy visual inspection under inverted microscope. Said cells have to be dissociated enzymatically (e.g. with trypsin). In addition, the growth of adherent cells is limited by surface area, which may limit product yields.

In preferred embodiments of the present invention, the non-adherent cells grow under serum-free conditions. The term "serum-free conditions", as used herein, refers to condition, wherein cells grow in medium which is devoid of animal serum. Instead, cells grow in medium devoid of any animal derived components and preferably in a medium without any complex mixtures of biologic components, a so called chemically defined medium.

Generally, non-adherent cell cultures are clonally maintained by the routine transfer (subculture) of cells in the early stationary phase to a fresh medium. During the incubation period, the biomass of the non-adherent cell cultures increases due to cell division and cell enlargement. This continues for a limited period since the viability of cells in suspension after the stationary phase decreases due to the exhaustion of some factors or the accumulation of toxic substances in the medium. At this stage an aliquot of the non-adherent cell culture with uniformly dispersed free cells and cell aggregates is transferred to afresh liquid medium of the original composition. During this process, the incubation period is important. The incubation period from culture initiation to the stationary phase is determined primarily by: a) initial cell density, b) duration of lag phase, and c) growth rate of cell line. While initiating a new non-adherent cell culture, it is necessary to determine optimal cell density, proportionate to the volume of the culture medium, in order to achieve maximum growth. Cell cultures initiated at very low densities will not grow unless the medium is enriched with the metabolites necessary to grow single cells or a small population of cells.

The non-adherent cell as described above may be any cell, wherein a fast cycling cdc42 mutant and/or a secreted protein can be expressed. It is preferred that the cell is an eukaryotic cell, preferably a vertebrate cell. It is particularly preferred that the vertebrate cell is a mammalian, a fish, an amphibian, a reptilian cell or an avian cell.

It is more preferred that (i) the mammalian cell is a human, mouse, rat, hamster, canine or monkey cell, more particularly a Chinese hamster ovary (CHO) cell, a Syrian hamster fibroblast (BHK21) cell (ATCC CCL-10), a SP2/0-Ag14 cell (ATCC CRL-1581), a NS0 cell (ECACC No. 85110503), a human cervical carcinoma (HELA) cell (ATCC CCL 2), a human PER.C6 cell, or a human AGE1.HN cell, (ii) the fish cell is a *Ictalurus punctatus* (channel catfish) cell, more particularly a *Ictalurus punctatus* (channel catfish) ovary (CCO) cell (ATCC CRL-2772), (iii) the amphibian cell is a *Xenopus laevis* cell, more particularly a *Xenopus laevis* kidney cell (ATCC CCL-102), (iv) the reptilian cell is an *Iguana iguana* cell, more particularly an *Iguana iguana* heart (IgH-2) cell (ATCC CCL-108), or (v) the avian cell is an avian retina cell, more particularly a AGE1.CR.PIX cell, or an avian somite cell.

The cell line AGE1.CR.PIX was deposited with the DSMZ-Deutsche Sammlung von Mikroorganismen und Zellkulturen GmbH, Mascheroder Weg 1b, 38124 Braunschweig, Germany on Nov. 24, 2005 under accession number DSM ACC2749. The cell line AGE1.HN was deposited with the DSMZ-Deutsche Sammlung von Mikroorganismen und Zellkulturen GmbH, Mascheroder Weg 1b, 38124 Braunschweig, Germany on Nov. 4, 2005 under accession number DSM ACC2744.

As described above, it is particularly preferred that the cell is a Chinese hamster ovary (CHO) cell. CHO cells are cells which were originally isolated in 1952. Said cells are used in their original form for cell biology research. Such cells grow adherent, attached to a solid surface in medium containing animal serum. The CHO cells, preferably used herein, are adapted to non-adherent cell culture. Because the original CHO cells would undergo apoptosis under serum-free conditions and in the absence of a suitable surface, this adaptation is a prolonged process requiring passaging with diminishing amounts of serum thereby selecting an irreversibly modified cell population (see above). Derivatives of parental lineage CHO pro- (specifically CHO-K1), preferably used herein, are independently adapted to serum-free suspension culture at several companies and gave rise to rather similar sublines of CHO-S and CHO-SV. One variant of this lineage, DUKX B11, is modified to contain only one allele of the dhfr gene that is inactivated by mutation. Another CHO subline, DG44, diverges earlier from the common ancestor and lacks both alleles of dhfr (Urlaub et al., 1986, Proc Natl Acad Sci USA. 83 (2): 337-341).

In most preferred embodiments of the present invention, the Chinese hamster ovary (CHO) cell is a CHO-K1 or CHO-DG44 cell.

CHO-K1 or CHO-DG44 cells are extensively applied in the production of recombinant proteins and antibodies. Despite the high flexibility of CHO cells in general, both CHO-K1 or CHO-DG44 cells have individual distinct features. CHO-K1 cells grow to higher peak cell densities, whereas DG44 cells usually show a higher specific productivity. Typically, media are not compatible between the two cell lineages. The method according to the invention has been successfully practiced in suspension adapted cells of both lineages: K1 (CHO-S obtained from LTC) and DG44 (specifically adapted to suspension culture by ProBioGen).

Preferred cell lines are summarized in the following Table 1:

translocation of the newly synthesized protein across the membrane of the endoplasmic reticulum (ER) in the cell. Said signal peptide usually serves as a marker for direct recognition by the signal recognition particle (SRP). Then, interaction of the SRP with the polypeptide on the ER allows for targeting of the nascent polypeptide-ribosome complex to the membrane of the ER. The signal peptide is subsequently released and the mature secretory protein is translocated in the ER. After translocation in the ER, the protein is secreted to the outside of the cell membrane via the Golgi apparatus, or the vacuoles. If the protein of interest does not naturally comprise the above-mentioned signal peptide, the polynucleotide comprising the nucleic acid sequence encoding said protein may further comprise a nucleic acid sequence encoding such a signal peptide.

Examples of desired secreted proteins include, but are not limited to, antibodies, enzymes, cytokines, lymphokines, adhesion proteins or fragments thereof, any polypeptide that can serve as agonist or antagonist. Specific examples of desired secreted proteins include, but are not limited to, insulin, insulin-like growth factor, hGH, tPA, cytokines, such as interleukines (IL), e.g. IL-I, IL-2, IL-3, IL-4, IL-5, IL-6, IL-7, IL-8, IL-9, IL-IO, IL-I 1, IL-12, IL-13, IL-14, IL-15, IL-16, IL-17, IL-18, interferon (IFN) alpha, IFN beta, IFN gamma, IFN omega or IFN tau, tumor necrosisfactor (TNF), such as TNF alpha and TNF beta, TNF gamma, TRAIL, G-CSF, GM-CSF, M-CSF, MCP-I and VEGF. Also included is the production of erythropoietin or any other hormone growth factor. Preferably, the afore-mentioned molecules have a therapeutic and/or diagnostic use.

The terms "antibody", "immunoglobulin", "Ig" and "Ig molecule" are used interchangeably in the context of the present invention. Included within the scope of said terms are classes of Igs, namely IgG, IgA, IgE, IgM, and IgD. Also included within the scope of said terms are the subtypes of IgGs, namely, IgG1, IgG2, IgG3 and IgG4. The terms are used in their broadest sense and include monoclonal antibodies (including full length monoclonal antibodies), polyclonal antibodies, single chain antibodies, and multispecific antibodies (e.g. bispecific antibodies). The term antibody also

TABLE 1

| CELL LINE | DEPOSITION NUMBER | ORIGIN |
| --- | --- | --- |
| NS0 | ECACC No. 85110503 | Mouse Myeloma |
| Sp2/0-Ag14 | ATCC CRL-1581 | Mouse Myeloma |
| BHK21 | ATCC CCL-10 | Baby Hamster Kindney |
| HELA | ATCC CCL 2 | Human cervical carcinoma |
| CHO | ECACC No. 8505302 | Chinese Hamster Ovary |
| CHO wild-type | ECACC 00102307 | Chinese Hamster Ovary |
| CHO-K1 | ATCC CCL-61 | Chinese Hamster Ovary |
| CHO-DUKX (=CHO duk⁻, CHO/dhfr⁻) | ATCC CRL-9096 | Chinese Hamster Ovary |
| CHO-DUKX B11 | ATCC CRL-9010 | Chinese Hamster Ovary |
| CHO-DG44 | not deposited at ATCC (Urlaub et al., 1983) | Chinese Hamster Ovary |
| CHO Pro-5 | ATCC CRL-1781 | Chinese Hamster Ovary |
| CHO-S | Invitrogen Cat No. 10743-029 | Chinese Hamster Ovary |

The term "secreted protein" (i.e. protein of interest or product of interest), as used herein, refers to any protein/polypeptide or protein/polypeptide fragment which can be expressed in the cell and which can leave the cell or is secreted by the cell. As mentioned above, the terms protein and polypeptide are interchangeably used herein.

The secreted protein may naturally comprise a signal sequence or non-naturally comprise a signal sequence (a so called signal peptide) which plays an important role in the includes scFv, dsFv, scFab, a single domain antibody, a maxibody, nanobody, transbody, diabody, adnectin, evibody, DARPin, affibody, ankyrin, iMab, camelid-antibody, glycosylated single-domain antigen-binding fragments derived from Camelid heavy chain-only antibodies, an engineered lipocalin-type protein such as an anticalin, an affilin, or a Kunitz-domain, knottin, followed by at least one, preferably two constant domains (Fc) of an immunoglobulin, preferably of human origin.

As mentioned above, it is preferred that the secreted protein is an exogenous protein. Preferably, the exogenous protein is selected from a group consisting of an antibody, an antibody fragment, a fusion protein, a glycoprotein, an enzyme, a cytokine, a lymphokine, an antigen and a hormone.

In a second aspect, the present invention relates to a method for preparing a non-adherent cell according to the first aspect comprising the following steps:
(i) providing a non-adherent cell or an adherent cell,
(ii) transfecting said cell with a polynucleotide comprising a nucleic acid sequence encoding a fast cycling cdc42 mutant, and
(iii) transfecting said cell with a polynucleotide comprising a nucleic acid sequence encoding a secreted protein,
wherein the adherent cell provided in step (i) is transferred into a non-adherent state after performance of step (ii) or (iii), and
wherein optionally, the cell of step (ii) or the cell of step (iii) is further transfected with a polynucleotide comprising an E1B gene region.

In other words, the present invention relates to a method for preparing a non-adherent cell according to the first aspect comprising the following steps:
(i) providing a non-adherent cell or an adherent cell,
(ii) transfecting said cell with a polynucleotide comprising a nucleic acid sequence encoding a fast cycling cdc42 mutant and optionally further transfecting said cell with a polynucleotide comprising an E1B gene region, and
(iii) transfecting said cell with a polynucleotide comprising a nucleic acid sequence encoding a secreted protein and optionally further transfecting said cell with a polynucleotide comprising an E1B gene region,
wherein the adherent cell provided in step (i) is transferred into a non-adherent state after performance of step (ii) or (iii).

It will be clear for the person skilled in the art that the optional feature of step (ii) and (iii), namely that said cell is further transfected with a polynucleotide comprising an E1B gene region, is only carried out once.

It may also be possible that the adherent cell transferred into a non-adherent state after performance of step (ii) is re-transferred into an adherent state before the performance of step (iii) and is after performance of step (iii) again transferred into a non-adherent state.

As to the definition of the terms "non-adherent", "adherent", and "fast cycling", it is referred to the first aspect of the invention. As to all preferred or particularly preferred embodiments regarding the cell, it is also referred to the first aspect of the invention.

Adherent cells and non-adherent cells are known in the art. The skilled person is aware of protocols for transferring a cell from an adherent state into a non-adherent state (see, for example, Appl Microbiol Biotechnol. 2008 March; 78(3): 391-9. Epub 2008 Jan. 9).

As mentioned above, non-adherent cells are preferably used for bulk protein production or batch harvesting, i.e. for protein production in industrial scale, where high protein yields are desired.

Preferably,
(a) steps (i), (ii), and (iii) are carried out in this order,
(b) steps (i), (iii) and (ii) are carried out in this order, or
(c) step (i) is carried out first and steps (ii) and (iii) are carried out next at the same time.

Depending on the sequence of the method steps chosen or depending on the transfection sequence used, the above-mentioned polynucleotides may be integrated into separate expression vectors or into one expression vector. For example, the polynucleotide comprising the nucleic acid sequence encoding the fast cycling cdc42 mutant, the polynucleotide comprising the nucleic acid sequence encoding the secreted protein and the polynucleotide comprising the E1B gene region may be integrated into separate expression vectors, e.g. transient expression vectors or vectors which integrate into the genome of the cell. Alternatively, said polynucleotides can be comprised in one expression vector. This could be, for example, the case where steps (ii) and (iii) are carried out at the same time and where all three polynucleotides are transfected. Suitable expression vectors comprise plasmids, cosmids, bacterial artificial chromosomes (BAC) and viral vectors. Preferably, non-viral expression vectors are used. The expression may be driven from one promoter, two promoters, or three promoters (e.g. a constitutive promoter such as a human translocation elongation factor 2 (EF2) promoter) which are preferably operably-linked to the respective nucleic acid sequences (see above).

It is particularly preferred that the polynucleotide comprising the nucleic acid sequence encoding the fast cycling cdc42 mutant and the polynucleotide comprising the E1B gene region are integrated into one expression vector. Particularly, said polynucleotides are integrated into one expression vector in form of an expression unit of the nucleic acid sequence encoding the fast cycling cdc42 mutant and the E1B gene region linked via an IRES element and under control of a constitutive promoter, e.g. a human translocation elongation factor 2 (EF2) promoter (see examples 2 and 3 below).

The expression vector(s) or the polynucleotide(s) may further comprise a selectable marker. The term "selectable marker", as used herein, refers to a gene produced into a cell that confers a trait suitable for artificial selection. There are several reporter genes which are used in molecular biology and genetic engineering to indicate the success of a transfection of foreign nucleic acids into a cell. Selectable markers are often antibiotic resistance genes. For example, cells that have been subjected to a procedure to introduce foreign nucleic acids are grown on a medium containing an antibiotic, and those cells that can grow have successfully taken up and expressed the introduced genetic material. As selectable marker, the neo gene from Tn5, which confers antibiotic resistance to geneticin, may be used. Alternatively, the expression vector(s) or the polynucleotide(s) may be equipped with a G418, puromycin, or neomycin resistance gene for direct selection of transfected cells.

The transfection may be performed according to standard procedures known to the person skilled in the art. Following the introduction of foreign nucleic acids, transfected cells may be selected by applying selective pressure by adding, for example, antibiotics, e.g. G418, puromycin, neomycin or geneticin, to the culture medium. As mention above, suitable selection systems are well known in the art.

In a third aspect, the present invention relates to a method for producing a secreted protein comprising the following steps:
(i) providing a non-adherent cell according to the first aspect,
(ii) culturing said cell, and
(iii) harvesting the secreted protein produced by said cell.

Culturing in step (ii) may be performed according to standard procedures readily available to the skilled person. In this respect, is should be noted that culture/incubation times are important for the production of secreted proteins in high yields. In addition, since the integral of viable cell density (IVCD) is one of the factors that impact the overall volumetric productivity in cell culture, it is desirable to keep cell viability at a high level over the duration of upstream processing. Further, nutrient depletion, extended exposure to impeller shear forces and other factors that occur during culturing may constitute apoptotic stimuli which serve to decrease cell viability and which should, thus, be avoided.

It is preferred that the culturing time ranges between 1 day and 24 days, more preferably between 3 and 24 days, most preferably between 5 and 24 days, e.g. 1, 2, 3, 4, 5, 6, 7, 8, 9, 10, 11, 12, 13, 14, 15, 16, 17, 18, 19, 20, 21, 22, 23, or 24 days.

Preferably, the cell is cultured in step (ii) in an agitated culture or in a bioreactor. Bioreactors are generally categorized similarly to chemical reactors according to their mixing characteristics. Said bioreactor may be a (well mixed) stirred tank reactor or a plug flow (tubular) reactor. In an ideal well-mixed bioreactor, the mixing is assumed to be intense enough that the fluid (cells and culture medium) is homogenous through the reactor.

In preferred embodiments, the bioreactor is a fed-batch, batch, or continuous bioreactor or the culturing is a batch, fed-batch or continuous culturing process.

A bioreactor is usually called continuous, when the feed and product streams are continuously being fed and withdrawn from the system. In principle, a reactor can have a continuous recirculating flow, but no continuous feeding of nutrient or product harvest; it is still a batch bioreactor. A fed-batch bioreactor usually has intermittent feed. It may or may not have medium withdrawal during the run.

The term "fed-batch culture", as used herein, may refer to a process of culturing cells in which a defined amount of cells is provided in a suitable culture medium and cultivated in suspension for a prolonged time (typically 8-20 days) during which time no medium is removed. However, additional components are provided to the culture at some time subsequent to the beginning of the culture process. The provided components typically comprise nutritional supplements for the cells that have been depleted during the culturing process. A fed-batch culture is typically stopped at a point where the ratio of living to dead cells drops below a critical value.

Various harvesting procedures are known in the art for proteins secreted from cells. An harvesting procedure which is useful according to the invention does not interfere with the secreted proteins to be harvested. For example, extended exposure to impeller shear forces and other factors that occur during harvesting should be avoided.

It is preferred that harvesting in step (iii) is achieved by separating the secreted protein from said cell via centrifugation, sedimentation and/or filtration, e.g. via centrifugation and filtration, via sedimentation and filtration, via sedimentation and centrifugation, or via centrifugation, sedimentation and filtration. Depending on the secreted protein to be harvested, the parameters for centrifugation, sedimentation or filtration may vary. The person skilled in the art is able to easily adapt the appropriate separation parameters, e.g. the acceleration-force/G-force and/or time using centrifugation for separation, filter size using filtration for separation, and/or sedimentation time using sedimentation for separation, in order to harvest the secreted protein produced by said cells.

In step (iii), which is preferably performed via centrifugation, sedimentation and/or filtration, the secreted protein (i.e. the protein of interest) is usually separated/isolated from the cell. After step (iii), further separation/isolation of the secreted protein may be required, preferably from the cell supernatant. Thus, it is preferred that the above method further comprises subsequent to step (iii) the step (iv) of purifying the secreted protein, preferably from the cell supernatant. In preferred embodiments, the purification is achieved via chromatography, preferably column chromatography, more preferably size exclusion chromatography, hydrophobic interaction chromatography, ion exchange chromatography, affinity chromatography, or high pressure liquid chromatography, electrophoresis, preferably gel electrophoresis, or ultracentrifugation.

As mentioned above (see first aspect), the polynucleotide which comprises the nucleic acid sequence encoding the secreted protein may further comprise a nucleic acid sequence encoding a tag. Said tag may facilitate the harvesting process and/or the purification process of the secreted proteins produced from the cell. It is preferred that said tag is removable after harvesting and/or purification by chemical agents or by enzymatic means, such as proteolysis. Said tag may be an affinity tag or epitope tag.

Affinity tags may be selected from the group consisting of chitin binding protein (CBP), maltose binding protein (MBP), and glutathione-S-transferase (GST). A FLAG tag or a poly(His) tag may also be used. A poly(His) tag is a widely-used protein tag. It binds to metal matrices. Epitope tags are short peptide sequences which are chosen because high-affinity antibodies can be reliably produced in many different species. These are usually derived from viral genes, which explain their high immunoreactivity. Epitope tags include V5-tag, c-myc-tag, and HA-tag. These tags are particularly useful for western blotting and immunoprecipitation experiments, although they also find use in antibody purification.

In a fourth aspect, the present invention relates to a non-adherent Chinese hamster ovary (CHO) cell comprising a polynucleotide comprising a nucleic acid sequence encoding a fast cycling cdc42 mutant.

Preferably, the Chinese hamster ovary (CHO) cell is a CHO-K1 or CHO-DG44 cell. Other suitable and preferred CHO cells have already been described with respect to the first aspect of the present invention.

It is preferred that the fast cycling cdc42 mutant is expressed from a polynucleotide stably maintained in the cell (e.g. either episomally or chromosomally). It is further preferred that the fast cycling cdc42 mutant is stably expressed from a polynucleotide stably maintained in the cell. The term "stable expression" has already been defined above.

The polynucleotide comprising the nucleic acid sequence encoding the fast cycling cdc42 mutant may be integrated into an expression vector which is used to transfect the cell. Suitable expression vectors have already been described with respect to the first aspect of the present invention.

The expression of the nucleic acid sequence encoding the fast cycling cdc42 mutant may be controlled by expression control sequences. As to the definition of the term "expression control sequences" and as to preferred embodiments of expression control sequences, it is referred to the first aspect of the present invention. It will only be noted at this place that in preferred embodiments, the nucleic acid sequence encoding the fast cycling cdc42 mutant is under control of a constitutive promoter, preferably under control of a human translocation elongation factor 2 (EF2) promoter.

The above mentioned polynucleotide may comprise a nucleic acid sequence encoding a tag, e.g. a tag which allows the detection of the fast cycling cdc42 mutant. Such tag may be a fluorescence tag, e.g. GFP or EGFP.

Preferably, the fast cycling cdc42 mutant is an exogenous protein. The term "exogenous protein" has already been defined above.

As to the specific definitions with respect to the terms "non-adherent" and "fast cycling" and as to preferred embodiments of the cdc42 mutant, it is also referred to the first aspect of the present invention.

In addition, all other preferred or particularly preferred embodiments described in the context of the cell according to the first aspect of the invention, are similarly preferred or particularly preferred in the context of the cell according to the fourth aspect of the invention.

In a fifth aspect, the present invention relates to a method for preparing a non-adherent Chinese ovary hamster (CHO) cell according to the fourth aspect comprising the following steps:
(i) providing a non-adherent or adherent Chinese ovary hamster (CHO) cell, and
(ii) transfecting said cell with a polynucleotide comprising a nucleic acid sequence encoding a fast cycling cdc42 mutant, and optionally further transfecting said cell with
a polynucleotide comprising an E1B gene region.
wherein the adherent cell provided in step (i) is transferred into a non-adherent state after performance of step (ii).

All preferred or particularly preferred embodiments described in the context of the cell according to the first and fourth aspect of the invention, or in the context of the method according to the second aspect of the invention, are similarly preferred or particularly preferred in the context of the method according to the fifth aspect of the invention.

In a further aspect, the present invention relates to a secreted protein prepared by the method according to the third aspect.

Various modifications and variations of the invention will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be encompassed by the present invention.

The following figures and examples are merely illustrative of the present invention and should not be construed to limit the scope of the invention as indicated by the appended claims in any way.

The amino acid sequences and nucleic acid sequences described herein are summarized as follows:

```
Amino acid sequence of the CDC42 variant F28L
                                        SEQ ID NO: 1
MQTIKCVVVGDGAVGKTCLLISYTTNKLPSEYVPTVFDNYAVTVMIGGEP

YTLGLFDTAGQEDYDRLRPLSYPQTDVFLVCFSVVSPSSFENVKEKWVPE

ITHHCPKTPFLLVGTQIDLRDDPSTIEKLAKNKQKPITPETAEKLARDLK

AVKYVECSALTQKGLKNVFDEAILAALEPPEPKKSRRCVLL

Codon-optimized nucleic acid sequence of the
CDC42 variant F28L
                                        SEQ ID NO: 2
ATGCAGACCATTAAGTGCGTGGTGGTCGGAGATGGCGCCGTGGGCAAGAC

CTGCCTGCTGATCTCCTACACCACCAACAAGCTGCCTTCCGAGTACGTGC

CCACCGTGTTCGACAACTACGCCGTGACCGTGATGATCGGCGGCGAGCCT

TACACCCTGGGCCTGTTCGACACCGCTGGCCAGGAAGATTACGACCGGCT

GCGGCCTCTGTCTTACCCTCAGACCGACGTGTTCCTGGTCTGCTTCTCCG

TGGTGTCCCCTAGCTCCTTCGAGAACGTGAAAGAAAAATGGGTGCCCGAG

ATCACCCACCACTGCCCTAAGACCCCTTTCCTGCTGGTCGGCACCCAGAT

CGACCTGCGGGACGACCCTTCCACCATCGAGAAGCTGGCCAAGAACAAGC

AGAAGCCTATCACCCCTGAGACAGCCGAAAAGCTGGCCCGGGACCTGAAG
```

```
GCCGTGAAATACGTGGAGTGCTCCGCCCTGACCCAGAAAGGCCTGAAGAA

CGTGTTCGACGAGGCCATCCTGGCCGCTCTGGAACCTCCTGAGCCTAAGA

AATCCCGGCGCTGCGTGCTGCTGTGATGA

Amino acid sequence of the 19K protein (small
protein) encoded by the Adenovirus 5 E1B region
                                        SEQ ID NO: 3
MEAWECLEDFSAVRNLLEQSSNSTSWFWRFLWGSSQAKLVCRIKEDYKWE

FEELLKSCGELFDSLNLGHQALFQEKVIKTLDFSTPGRAAAAVAFLSFIK

DKWSEETHLSGGYLLDFLAMHLWRAVVRHKNRLLLLSSVRPAIIPTEEQQ

QQQEEARRRQEQSPWNPRAGLDPRE

Amino acid sequence of the 55K protein (large
protein) encoded by the Adenovirus 5 E1B region
                                        SEQ ID NO: 4
MERRNPSERGVPAGFSGHASVESGCETQESPATVVFRPPGDNTDGGAAAA

AGGSQAAAAGAEPMEPESRPGPSGMNVVQVAELYPELRRILTITEDGQGL

KGVKRERGACEATEEARNLAFSLMTRHRPECITFQQIKDNCANELDLLAQ

KYSIEQLTTYWLQPGDDFEEAIRVYAKVALRPDCKYKISKLVNIRNCCYI

SGNGAEVEIDTEDRVAFRCSMINMWPGVLGMDGVVIMNVRFTGPNFSGTV

FLANTNLILHGVSFYGFNNTCVEAWTDVRVRGCAFYCCWKGVVCRPKSRA

SIKKCLFERCTLGILSEGNSRVRHNVASDCGCFMLVKSVAVIKHNMVCGN

CEDRASQMLTCSDGNCHLLKTIHVASHSRKAWPVFEHNILTRCSLHLGNR

RGVFLPYQCNLSHTKILLEPESMSKVNLNGVFDMTMKIWKVLRYDETRTR

CRPCECGGKHIRNQPVMLDVTEELRPDHLVLACTRAEFGSSDEDTD

Amino acid sequence of the CDC42 variant D118N
                                        SEQ ID NO: 5
MQTIKCVVVGDGAVGKTCLLISYTTNKFPSEYVPTVFDNYAVTVMIGGEP

YTLGLFDTAGQEDYDRLRPLSYPQTDVFLVCFSVVSPSSFENVKEKWVPE

ITHHCPKTPFLLVGTQINLRDDPSTIEKLAKNKQKPITPETAEKLARDLK

AVKYVECSALTQKGLKNVFDEAILAALEPPEPKKSRRCVLL

Amino acid sequence of the CDC42
variant F28L/D121N
                                        SEQ ID NO: 6
MQTIKCVVVGDGAVGKTCLLISYTTNKLPSEYVPTVFDNYAVTVMIGGEP

YTLGLFDTAGQEDYDRLRPLSYPQTDVFLVCFSVVSPSSFENVKEKWVPE

ITHHCPKTPFLLVGTQIDLRNDPSTIEKLAKNKQKPITPETAEKLARDLK

AVKYVECSALTQKGLKNVFDEAILAALEPPEPKKSRRCVLL

E1B gene region, Adenovirus 5
                                        SEQ ID NO: 7
ATGGAGGCTTGGGAGTGTTTGGAAGATTTTTCTGCTGTGCGTAACTTGCT

GGAACAGAGCTCTAACAGTACCTCTTGGTTTTGGAGGTTTCTGTGGGCT

CATCCCAGGCAAAGTTAGTCTGCAGAATTAAGGAGGATTACAAGTGGGAA

TTTGAAGAGCTTTTGAAATCCTGTGGTGAGCTGTTTGATTCTTTGAATCT

GGGTCACCAGGCGCTTTTCCAAGAGAAGGTCATCAAGACTTTGGATTTTT

CCACACCGGGGCGCGCTGCGGCTGCTGTTGCTTTTTTGAGTTTTATAAAG

GATAAATGGAGCGAAGAAACCCATCTGAGCGGGGGGTACCTGCTGGATTT

TCTGGCCATGCATCTGTGGAGAGCGGTTGTGAGACACAAGAATCGCCTGC
```

-continued
```
TACTGTTGTCTTCCGTCCGCCCGGCGATAATACCGACGGAGGAGCAGCAG

CAGCAGCAGGAGGAAGCCAGGCGGCGGCGGCAGGAGCAGAGCCCATGGAA

CCCGAGAGCCGGCCTGGACCCTCGGGAATGAATGTTGTACAGGTGGCTGA

ACTGTATCCAGAACTGAGACGCATTTTGACAATTACAGAGGATGGGCAGG

GGCTAAAGGGGGTAAAGAGGGAGCGGGGGGCTTGTGAGGCTACAGAGGAG

GCTAGGAATCTAGCTTTTAGCTTAATGACCAGACACCGTCCTGAGTGTAT

TACTTTTCAACAGATCAAGGATAATTGCGCTAATGAGCTTGATCTGCTGG

CGCAGAAGTATTCCATAGAGCAGCTGACCACTTACTGGCTGCAGCCAGGG

GATGATTTTGAGGAGGCTATTAGGGTATATGCAAAGGTGGCACTTAGGCC

AGATTGCAAGTACAAGATCAGCAAACTTGTAAATATCAGGAATTGTTGCT

ACATTTCTGGGAACGGGCCGAGGTGGAGATAGATACGGAGGATAGGGTG

GCCTTTAGATGTAGCATGATAAATATGTGGCCGGGGGTGCTTGGCATGGA

CGGGGTGGTTATTATGAATGTAAGGTTTACTGGCCCCAATTTTAGCGGTA

CGGTTTTCCTGGCCAATACCAACCTTATCCTACACGGTGTAAGCTTCTAT

GGGTTTAACAATACCTGTGTGGAAGCCTGGACCGATGTAAGGGTTCGGGG

CTGTGCCTTTTACTGCTGCTGGAAGGGGTGGTGTGTCGCCCCAAAAGCA

GGGCTTCAATTAAGAAATGCCTCTTTGAAAGGTGTACCTTGGGTATCCTG

TCTGAGGGTAACTCCAGGGTGCGCCACAATGTGGCCTCCGACTGTGGTTG

CTTCATGCTAGTGAAAAGCGTGGCTGTGATTAAGCATAACATGGTATGTG

GCAACTGCGAGGACAGGGCCTCTCAGATGCTGACCTGCTCGGACGGCAAC

TGTCACCTGCTGAAGACCATTCACGTAGCCAGCCACTCTCGCAAGGCCTG

GCCAGTGTTTGAGCATAACATACTGACCCGCTGTTCCTTGCATTTGGGTA

ACAGGAGGGGGTGTTCCTACCTTACCAATGCAATTTGAGTCACACTAAG

ATATTGCTTGAGCCCGAGAGCATGTCCAAGGTGAACCTGAACGGGGTGTT

TGACATGACCATGAAGATCTGGAAGGTGCTGAGGTACGATGAGACCCGCA

CCAGGTGCAGACCCTGCGAGTGTGGCGGTAAACATATTAGGAACCAGCCT

GTGATGCTGGATGTGACCGAGGAGCTGAGGCCCGATCACTTGGTGCTGGC

CTGCACCCGCGCTGAGTTTGGCTCTAGCGATGAAGATACAGATTGAGG
```

Amino acid sequence of the wild-type CDC42 protein from Mus musculus (AAC00028)

SEQ ID NO: 8

MQTIKCVVVGDGAVGKTCLLISYTTNKFPSEYVPTVFDNYAVTVMIGGEP

YTLGLFDTAGQEDYDRLRPLSYPQTDVFLVCFSVVSPSSFENVKEKWVPE

ITHHCPKTPFLLVGTQIDLRDDPSTIEKLAKNKQKPITPETAEKLARDLK

AVKYVECSALTQKGLKNVFDEAILAALEPPEPKKSRRCVLL

EXAMPLES

Figure 1:
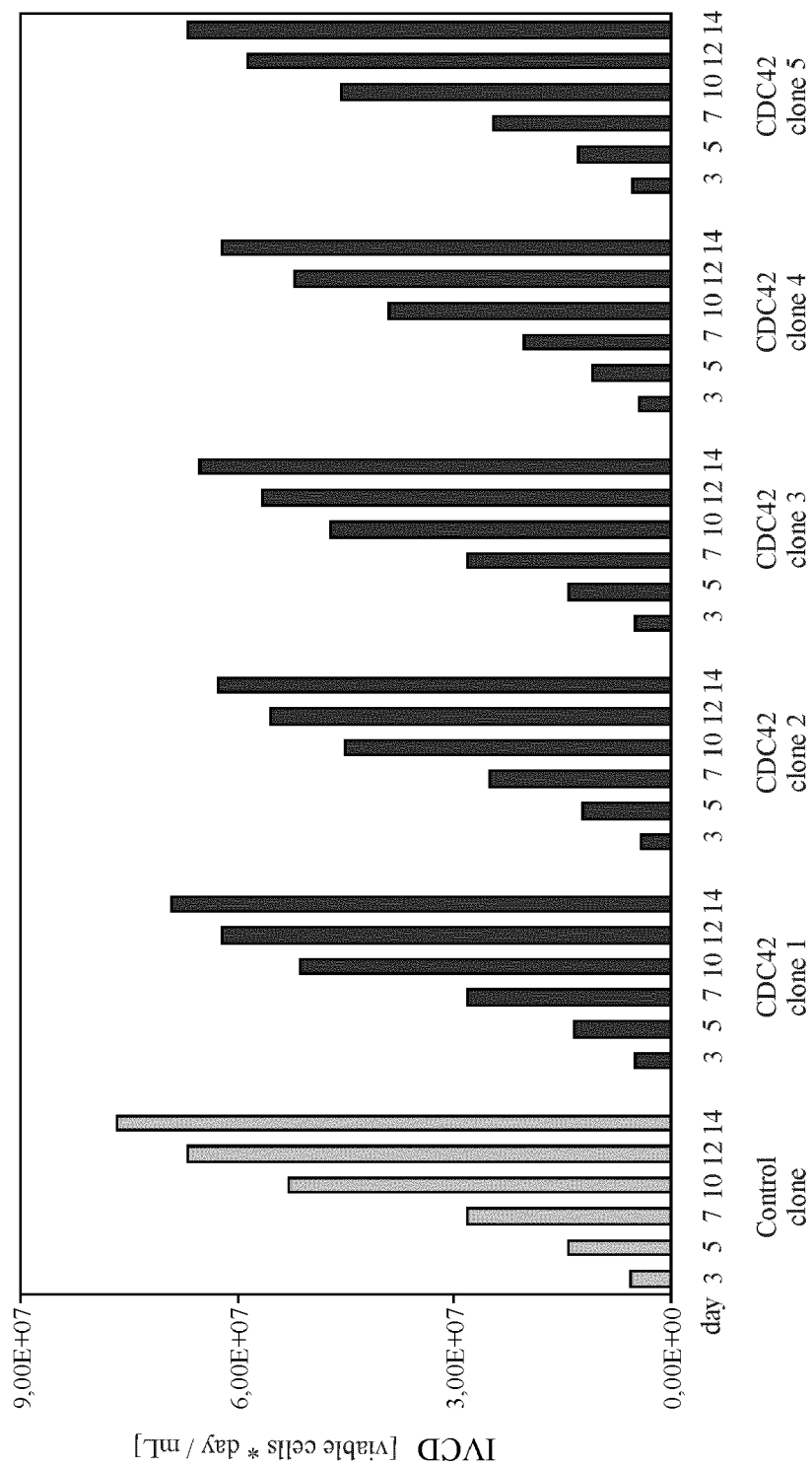
FIG. 1: Shows the cumulative integrated viable cell densities (IVCDs) of the control CHO-IgG clone and five CDC42F28L engineered CHO-IgG clones in shaken fed-batch culture over 14 days. Abbreviations: CDC42=CDC42F28L fast cycling mutant, IVCD=integrated viable cell density.

The examples are designed in order to further illustrate the present invention and serve a better understanding. They are not to be construed as limiting the scope of the invention in any way.

Example 1

The example describes the effect of heterologous CDC42F28L expression on growth properties and productivity of a pre-existing antibody producer line.

Cell Lines

The recombinant cell line CHO-DG44-IgG was established by stable transfection of the dihydrofolate reductase-deficient CHO cell line, CHO/DG44 with an expression vector PBGABEX2 containing expression cassettes comprising nucleotide sequences encoding light and heavy chain of the therapeutic monoclonal antibody. The cell line has undergone two subsequent cloning rounds ensuring clonality and homogenetity of expression within this clone. Generation of the CDC42F28L engineered cell lines started from this pre-existing producer clone. The cell line was maintained in serum-free medium C8862 (SAFC).

Design of the CDC42F28L Gene

The amino acid sequence for CDC42 was deduced from the mouse sequence (GenBank Accession No. GenBank: AAC00028.1-191 amino acids). The sequence was reverse translated, the phenylalanine at position 28 was exchanged for leucine and the resulting nucleotide sequence optimized by knockout of cryptic splice sites and RNA destabilizing sequence elements, optimization for increased RNA stability and adaptation of codon usage to match the requirements of CHO cells (Cricetulus griseus).

Construction of a Vector Suitable for Co-Expression of CDC42F28L and Gfp

The synthesized CDC42F28L gene was excised from vector 0930044_PBG-M1_pMA with EcoRI and XhoI. The insert was ligated into bicistronic expression vector EF2-gfpN1 digested with EcoRI and XhoI which allows coordinated co-expression of CDC42F28L and green fluorescent protein from a bicistronic message (gfp). The resulting expression plasmid EF2-M1-gfpN1 is equipped with a Neomycin resistance gene allowing for direct selection of cells that have stably integrated the bicistronic expression cassette. General procedures for constructing expression plasmids are described in Sambrook, J., E. F. Fritsch and T. Maniatis: Cloning I/II/III, A Laboratory Manual New York/Cold Spring Harbor Laboratory Press, 1989, Second Edition.

Engineering of Antibody-Producing CHO-IgG Cells with CDC42F28L

CHO-DG44-IgG cells were stably transfected with expression vector EF2-M1-gfpN1 comprising the CDC42F28L and gfp by electroporation according to the manufacturer's instructions (MicroPorator, PEQLAB Biotech, Germany). After 24 h transfectants were selected in alpha-MEM containing the antibiotic G418. The G418-resistant clones were then isolated by limiting dilution cloning, i.e. they were resuspended in this selective medium and seeded into 96 well plates at dilutions where the likelihood of obtaining a colony from a single cell is greater 95% based on Poisson Statistics. After single cell cloning five clones expressing different levels of GFP were expanded into larger volumes and adapted to growth in suspension.

Clone Screening by Fluorescence Microscopy

Single cell clones growing in 96 well plates were screened for stable vector integration and CDD42F28L expression by monitoring of the GFP-fluorescence using an Olympus IX-50 (Olympus Optical Co., Europe) fitted with a c-mount adapter. For single cell clone screening a fluorescence-filter at 100-fold extension was used versus phase contrast.

RT-PCR Analysis for CDC42F28L Expression

For the chosen engineered clones CDC42F28L expression was analyzed by RT-PCR analysis. Total-RNA was prepared from exponential growing cultures (innuPREP RNA Mini Kit, Analytic Jena) and transcribed to cDNA with Random Hexamer Primers (Cloned AMV First-Strand cDNA Synthesis Kit, Invitrogen) according to manufacturer instructions. CDC42F28L expression was confirmed for all clones by RT-PCR (StepOnePlus Real-Time PCR System, Applied Biosystems) from cDNA samples using CDC42-specific primers and probes.

IgG1 Production from CDC42F28L Engineered Compared to Control Cells

In order to study the effects of CDC42F28L expression on product titer and specific productivity, the original CHO-DG44-IgG producer clone and the chosen CHO-DG44-IgG clones engineered to express various levels of CDC42F28L and gfp were analysed in parallel shaken fed-batch culture. The cell lines were used to produce IgG1 antibodies in the culture supernatant. Shake tube cultures were inoculated at 2×105 cells/mL in serum-free culture medium and incubated at 180 rpm, 37° C., 7.5% pCO2. Specific feed was applied every two days and cultures were stopped after 14 days.

Viable cell density was measured with an automatic cell counter, Vi-CELL™ XR (Beckman Coulter, Fullerton, Calif.), using trypan blue exclusion. Cell free culture supernatants were analyzed for antibody concentration by a Sandwich Immuno Assay specific for human IgG1 with the Gyrolab Workstation (Gyros AB, Sweden).

Unexpectedly, for most of the clones carrying CDC42F28L the integral viable cell density in chemically defined medium sharply declines compared to starter cells. (FIG. 1). This contradicts the results reported by Tu et al. (Tu 2002) who observed accelerated growth in medium containing a reduced serum concentration of 1%.

Figure 2:
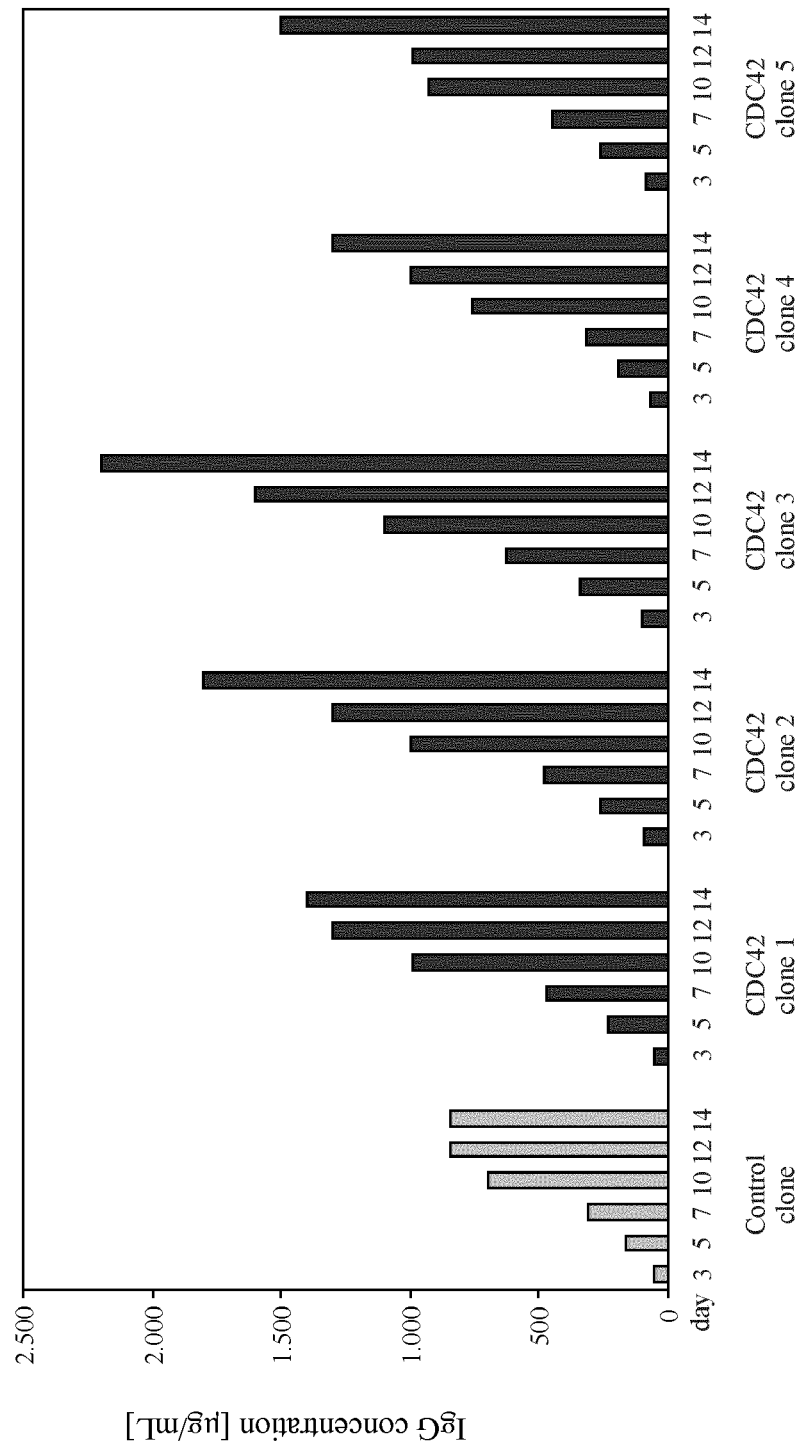
FIG. 2: Shows the cumulative IgG concentrations of the supernatant for the control CHO-IgG clone and five CDC42F28L engineered CHO-IgG clones in shaken fed-batch culture over 14 days. Abbreviations: CDC42=CDC42F28L fast cycling mutant.
Figure 3:
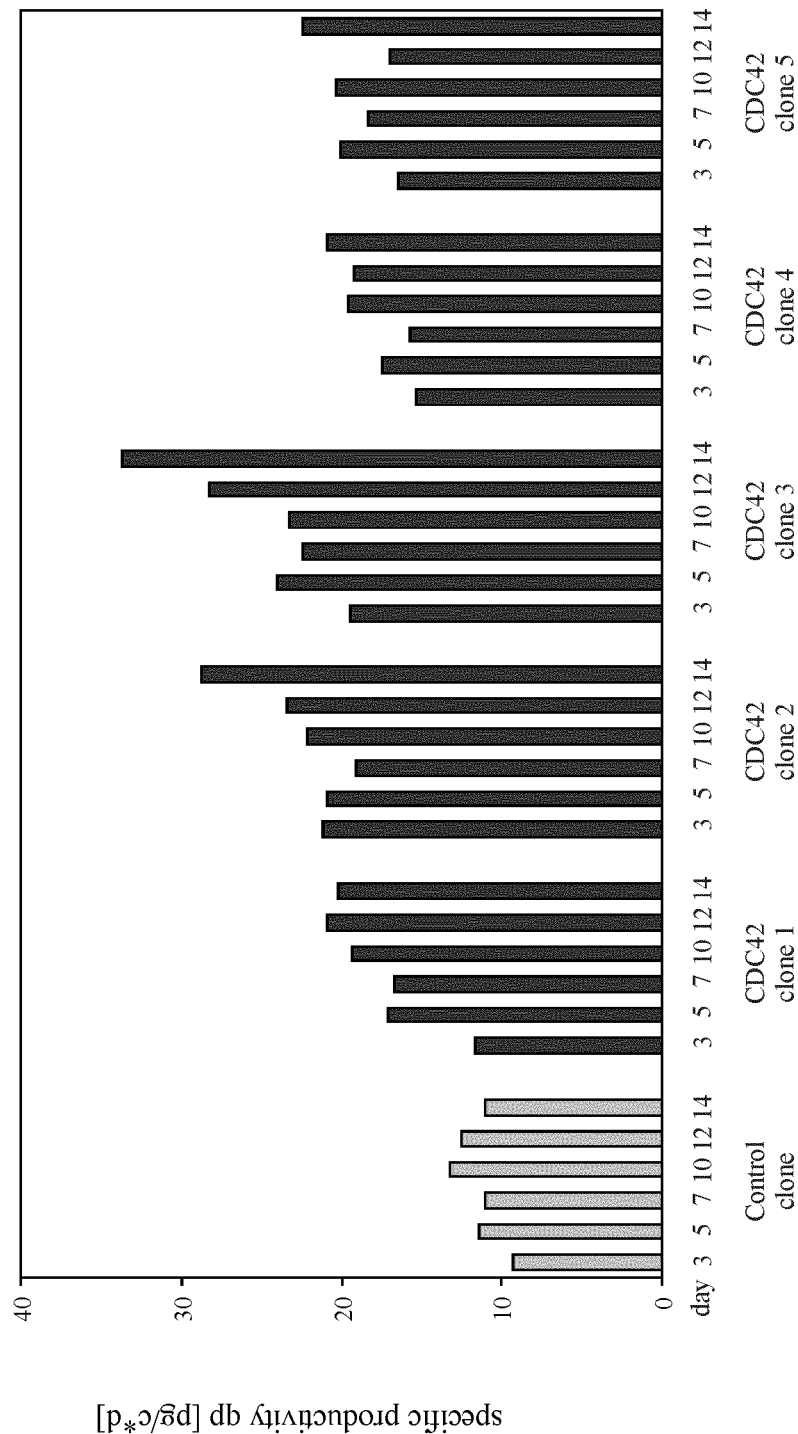
FIG. 3: Shows the specific IgG productivities for the control CHO-IgG clone and five CDC42F28L engineered CHO-IgG clones in shaken fed-batch culture over 14 days. Abbreviations: CDC42=CDC42F28L fast cycling mutant.

Antibody concentration was substantially (up to 2 fold) higher for all CDC42F28L engineered CHO-IgG clones (FIG. 2). Since the engineered clones showed a decline of the integral of viable cell density, the titer increase must have resulted from an increased specific productivity: Indeed, Cell specific productivity increases as well in all engineered clones, in particular during the later stages of the fed-batch culture for the engineered clones (FIG. 3).

The effect is conserved in clones that were chosen to express heterogenous amounts of CDC42F28L. Consequently, introduction of CDC42F28L into preexisting producer clones and its stable expression at various levels results in significantly enhanced antibody expression in a fed-batch process.

Example 2

The example describes the generation of starter cell lines of the CHO-K1 lineage engineered for expression of CDC42F28L or for joint expression of CDC42F28L and E1B of a C-group adenovirus. It also describes the application of these starter cell lines compared to naïve starter cells to generation of high producer lines and the effect of the different starter cell lines on productivity.

Cell Lines

The development started from CHO-S cells, a CHO K1 derivative, adapted to suspension culture with a known linage history (Life Technologies, US). In a first step, these cells were stably transfected to express the CDC42F28L alone or CDC42F28L in combination with the E1B of adenovirus 5 to generate engineered starter cell lines. The cell lines were cultivated in chemically defined medium in suspension.

Construction of the CDC42F28L Expression Plasmid

The expression plasmid EF2-M1-gfpN1 contains a bicistronic expression cassette encoding for CDC42F28L and gfp (see example 1) For removal of gfp the vector EF2-M1-gfpN1 was digested with NotI, 5' extruding ends were blunted with Klenow enzyme and a Klenow treated EcoRr1 Fragment from the same vector was inserted to re-establish the full expression unit of CDC42F28L resulting in EF2CDC42F28L. In this vector CDC42F28L is driven by the housekeeping promoter of the human EF2 gene. The vector is still equipped with an SV40 promoter driven Neomycin resistance gene allowing for direct selection of cells.

Construction of the Plasmid for Co Expression of CDC42F28L and E1B

EF2-M1-gfpN1 was digested with EcorI+HpaI to remove gfp together with the SV40 poly A. It was replaced by a PmeI, HincII fragment from plasmid Ad5E1AB encoding the entire natural sequence of the transcribed E1B region from human C group adenovirus type 5 followed by a tk polyadenylation signal. With the exception of single point mutations this region is identical between all human C group adenoviruses, namely Adenovirus 2, 5 and 6. The resulting plasmid EF2CD42F28LE1B contains the expression unit of CDC42F28L and E1B linked via an IRES element and driven by the housekeeping promoter of the human EF2 gene.

Engineering of CHO-S Cells with CDC42F28L and CDC42F28L/E1B

CHO-S cells were stably transfected with expression vectors EF2CDC42F28L or EF2CD42F28LE1B by electroporation as described above (Example 1). After 24 h transfectants were seeded in 96 well plates and selected in medium containing the antibiotic G418 to obtain either single cell clones or multiple clones per well. G418-resistant single cell clones were directly expanded. 96 well plates with multiple G418-resistant clones per well were pooled and single cell clones were isolated by limiting dilution cloning as described above (Example 1). After single cell cloning 30 clones engineered with CDC42F28L and 30 clones engineered with CDC42F28L/E1B were chosen according to their growth properties and expanded for further characterization.

RT-PCR Analysis of Stable CDC42F28L and E1B Expression

For the chosen engineered clones, stability of CDC42F28L and E1B expression was confirmed by RT-PCR analysis. RNA preparation, cDNA synthesis and RT-PCR were done as described above (Example 1). CDC42F28L and E1B expression were analyzed from cDNA samples using CDC42- or E1B-specific primers and probes.

Analysis of Cell Viability and Growth for the Chosen Engineered CDC42F28L- and CDC42F28L/E1B Clones in Serum-Free Fed-Batch Culture In order to study the effects of CDC42F28L and E1B expression on cell viability and IVCD, CHO-S cells and the chosen CDC42F28L- and CDC42F28L/E1B-engineered clones were analyzed in parallel shaken fed-batch culture. Shake tube cultures were inoculated at $3\times10^5$ cells/mL in chemically defined culture medium and incubated at 180 rpm, 37° C., 7.5% $pCO_2$. Glucose feed was applied every two days and cultures were stopped after 12 days. Viable cell density was measured as described for Example 1.

Figure 4:
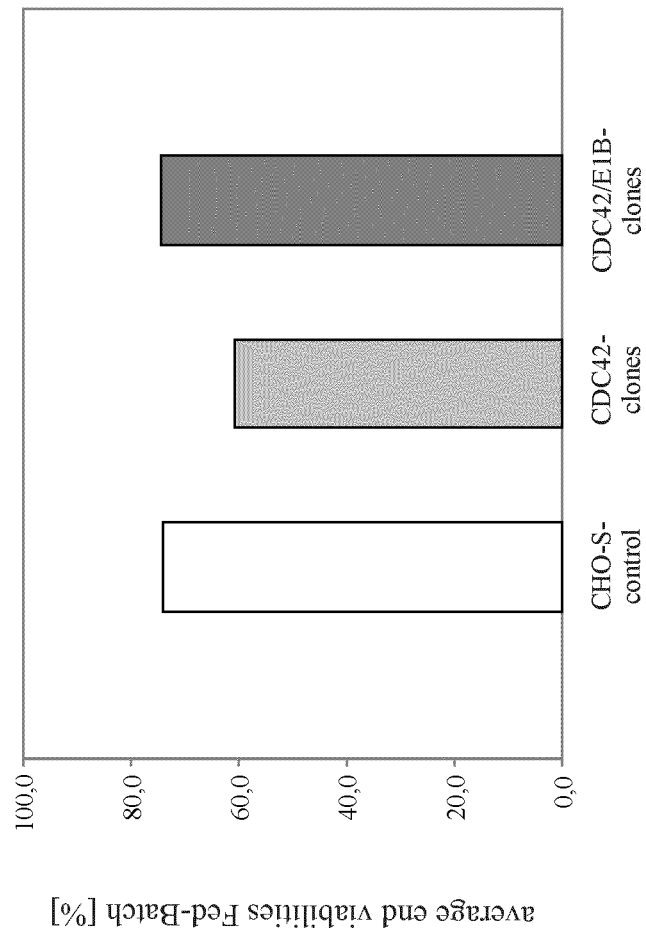
FIG. 4: Shows the end viabilities for the parental CHO-S control cells, and the average of 30 selected clones engineered either with CDC42F28L alone or in combination with E1B after 12 days in shaken fed-batch culture. Abbreviations: CDC42=CDC42F28L fast cycling mutant.
Figure 5:
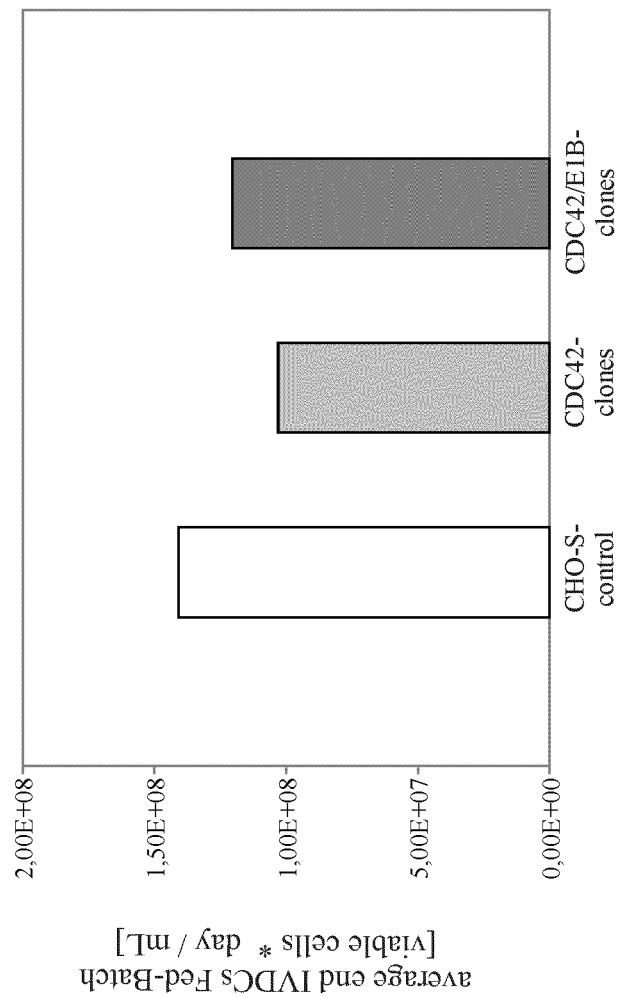
FIG. 5: Shows the cumulated end IVCDs for the parental CHO-S control cells, and the average of 30 selected clones engineered either with CDC42F28L alone or in combination with E1B in shaken fed-batch culture. Abbreviations: CDC42=CDC42F28L fast cycling mutant, IVCD=integrated viable cell density.

Compared to the control CHO-S cells, average end viabilities and IVCDs of the 30 CDC42F28L-engineered clones were found to be significantly lower (FIG. 4). Again, this contrasts the observations of Tu et al. (Tu 2002). Average end viabilities and IVCDs of the 30 engineered clones containing both CDC42F28L and E1B units were higher than obtained for the CDC42F28L-engineered clones alone (FIG. 4 and FIG. 5). Compared to the CHO-S control cells similar average end viabilities were observed for the E1B co-expressing clones (FIG. 4). In contrast, average IVCDs stayed still well below the CHO-S control cells (FIG. 5). Consequently, CDC42F28L-expression significantly lowered cell viabilities and growth. While E1B expression did fully compensate for the CDC42F28L-effects on cell viabilities, cell growth was still affected to a certain extent. The 15 candidates with highest end viabilities and IVCDs for each, CDC42F28L- and CDC42F28L/E1B-engineered clones were selected for further characterization.

Transient Transfection of CDC42F28L- and CDC42F28L/E1B-Engineered Clones and Selection of Engineered Host Cell Candidates In order to reduce the number of selected host cell candidates, the chosen CDC42F28L and CDC42F28L/E1B clones and the parental CHO-S cells were subjected to transient transfection with an expression vector comprising the IgG1 therapeutic antibody Bevacizumab. Cells were transfected by electroporation as described above and transfectants were seeded in shake tubes to produce IgG1 antibodies in the culture supernatant for 72 h (180 rpm, 37° C., 7.5% $pCO_2$). Cell free culture supernatants were analyzed for antibody concentration as described for Example 1. Three candidates of each, CDC42F28L- and CDC42F28L/E1B-expressing clones were selected for higher product yields in this short term transient assay, as well as superior growth and viability profiles in Fed-batch were selected for further analysis by generation of stable antibody producers.

Long-Term Analysis of CDC42F28L and E1B Expression

Figure 6:
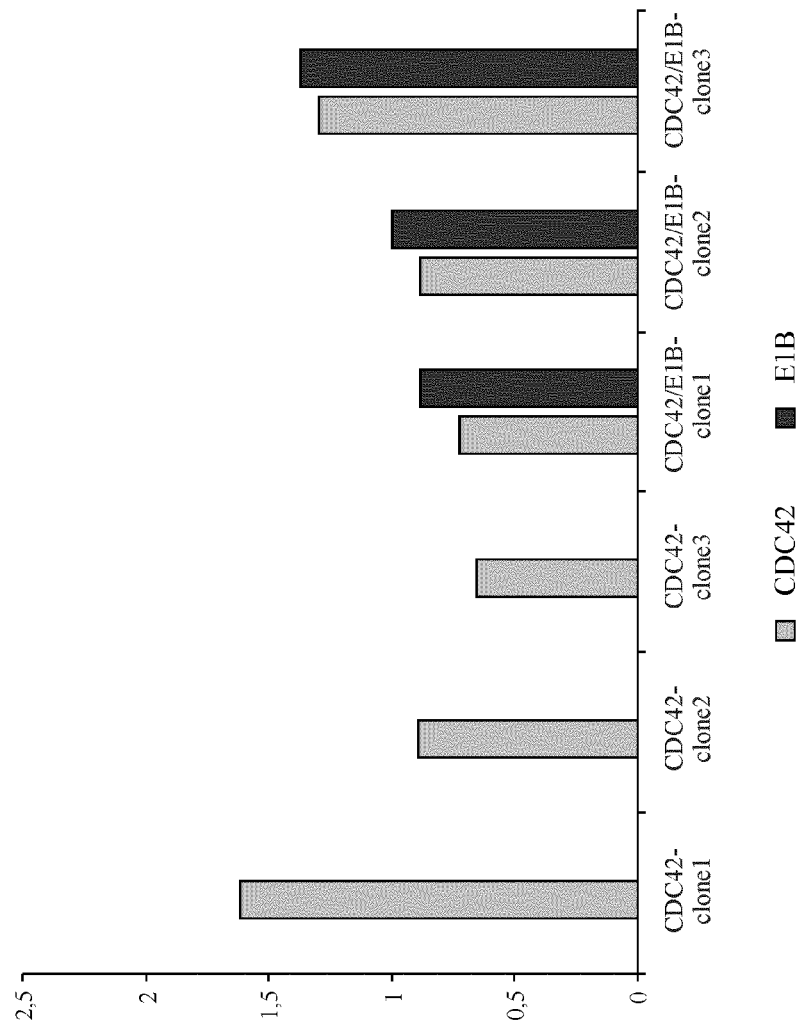
FIG. 6: Shows the relative CDC42F28L and E1B expression (determined by RT-PCR) for the chosen engineered CHO-S clones after 83 to 99 population doublings. Abbreviations: CDC42=CDC42F28L fast cycling mutant.

Long-term stability of CDC42F28L and E1B expression was analyzed for the selected engineered clones by RT-PCR (FIG. 6). Cells were passed for a minimum of 83 population doublings and RNA-samples were generated at start and end-point of the study. RNA preparation, cDNA synthesis and RT-PCR were done as described above. Expression of CDC42F28L and E1B expression (for those clones containing both units) were maintained in all clones. Differences between the starting expression level and that obtained after 83 population doublings were not statistically significant. The interval studied is sufficient to confirm stability of the CDC42F28L and E1B units for a producer clones, because less than 60 population doublings are required for a clone to progress from an early premaster cell bank through the production window until the end of production leaving more than 20 population doublings for the establishment of such producer.

Generation of Stable Cell Lines and Production of IgG1 in Shaker Fed-Batch

In order to study the potential of engineered host cells, the selected CDC42F28L and CDC42F28L/E1B clones as well as the parental CHO-S cells were used to generate producer cell lines stably expressing an IgG1-type therapeutic antibody (Bevacizumab). The different host cells were stably transfected with an expression vector comprising the nucleotide sequences encoding light and heavy chain of this antibody. After 48 h transfectants were selected in medium containing the antibiotics puromycin and MTX, and resistant cells were isolated by limiting dilution cloning as described above (Example 1). For each engineered host cell candidate and parental CHO-S 100 single cell clones were screened for IgG-expression level and top 30 IgG clones were expanded. Those IgG clones were re-analyzed for IgG-expression in 24 well plates. The top 3 IgG clones from each of the starter cells were further expanded and compared in parallel shaken fed-batch culture. Shake flask cultures were inoculated at $3\times10^5$ cells/mL in chemically defined culture medium and incubated at 150 rpm, 37° C., 7.5% $pCO_2$. Glucose feed was applied every two days and cultures were stopped after 14 days.

Figure 7:
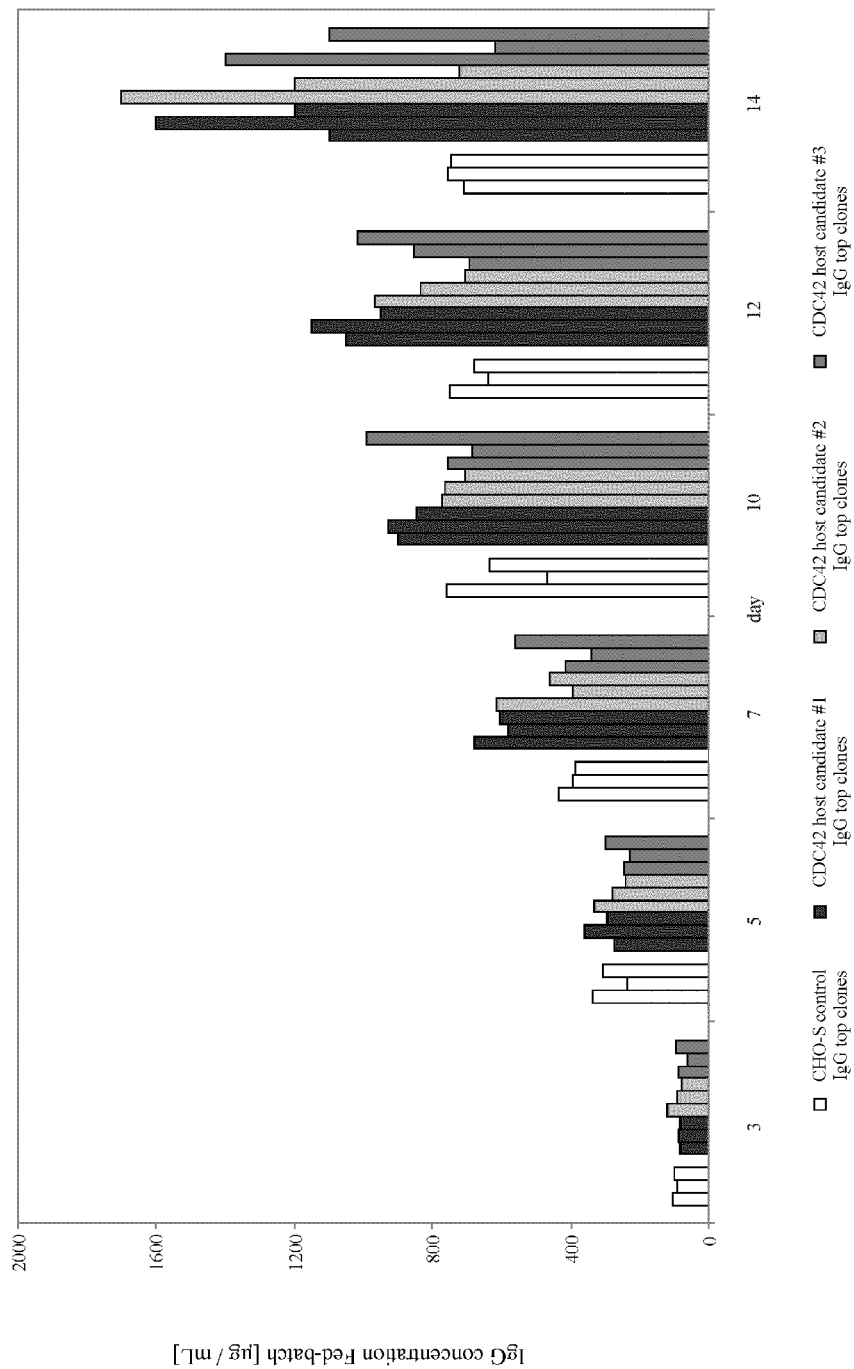
FIG. 7: Shows the cumulative IgG concentrations of the supernatant for the top 3 CHO-S control IgG clones and CDC42F28L engineered IgG clones in shaken fed-batch culture over 14 days. Abbreviations: CDC42=CDC42F28L fast cycling mutant.
Figure 8:
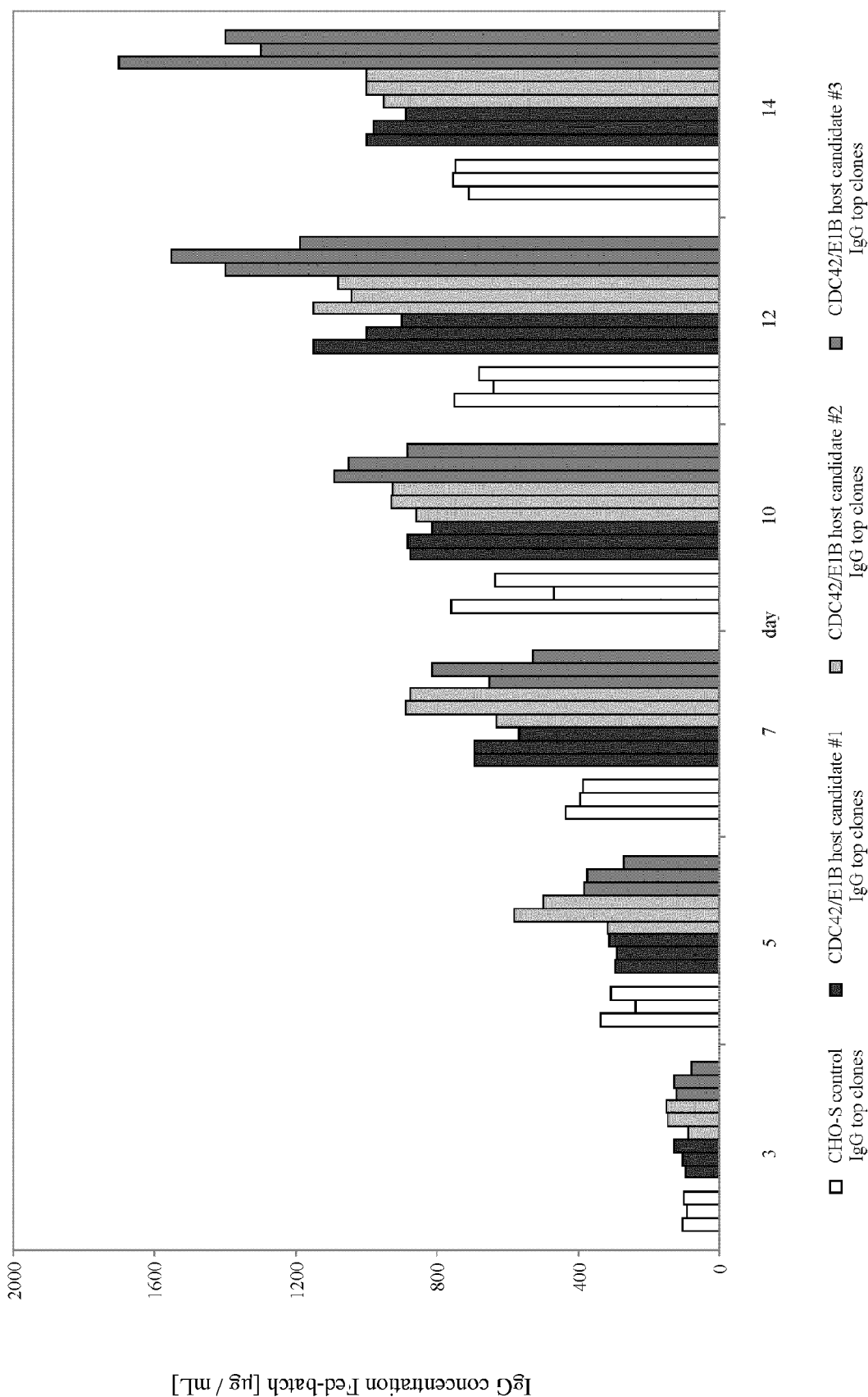
FIG. 8: Shows the cumulative IgG concentrations of the supernatant for the top 3 CHO-S control IgG clones and CDC42F28L/E1B engineered IgG clones in shaken fed-batch culture over 14 days. Abbreviations: CDC42=CDC42F28L fast cycling mutant.
Figure 9:
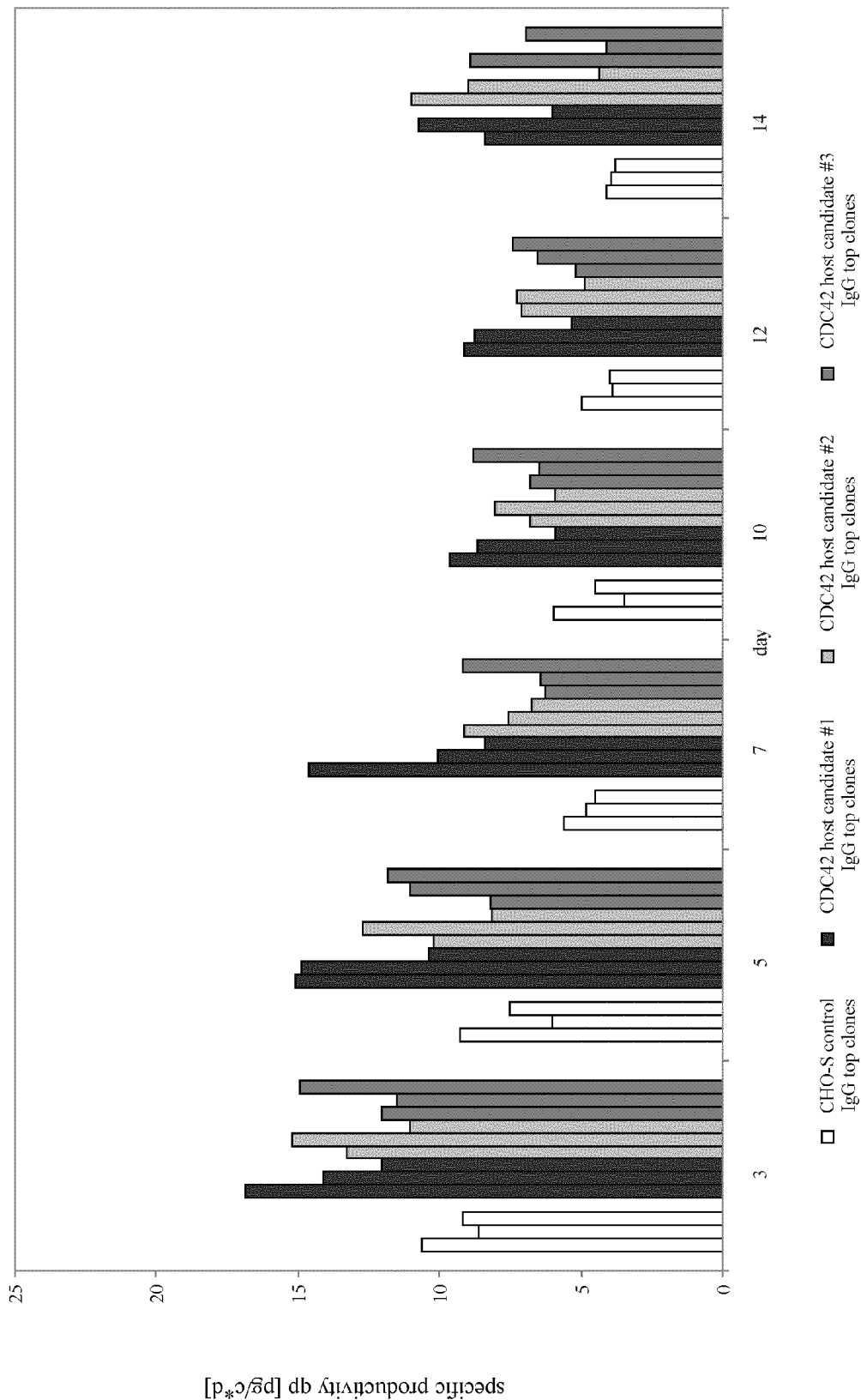
FIG. 9: Shows the specific IgG productivities for the top 3 CHO-S control IgG clones and CDC42F28L engineered IgG clones in shaken fed-batch culture over 14 days. Abbreviations: CDC42=CDC42F28L fast cycling mutant.
Figure 10:
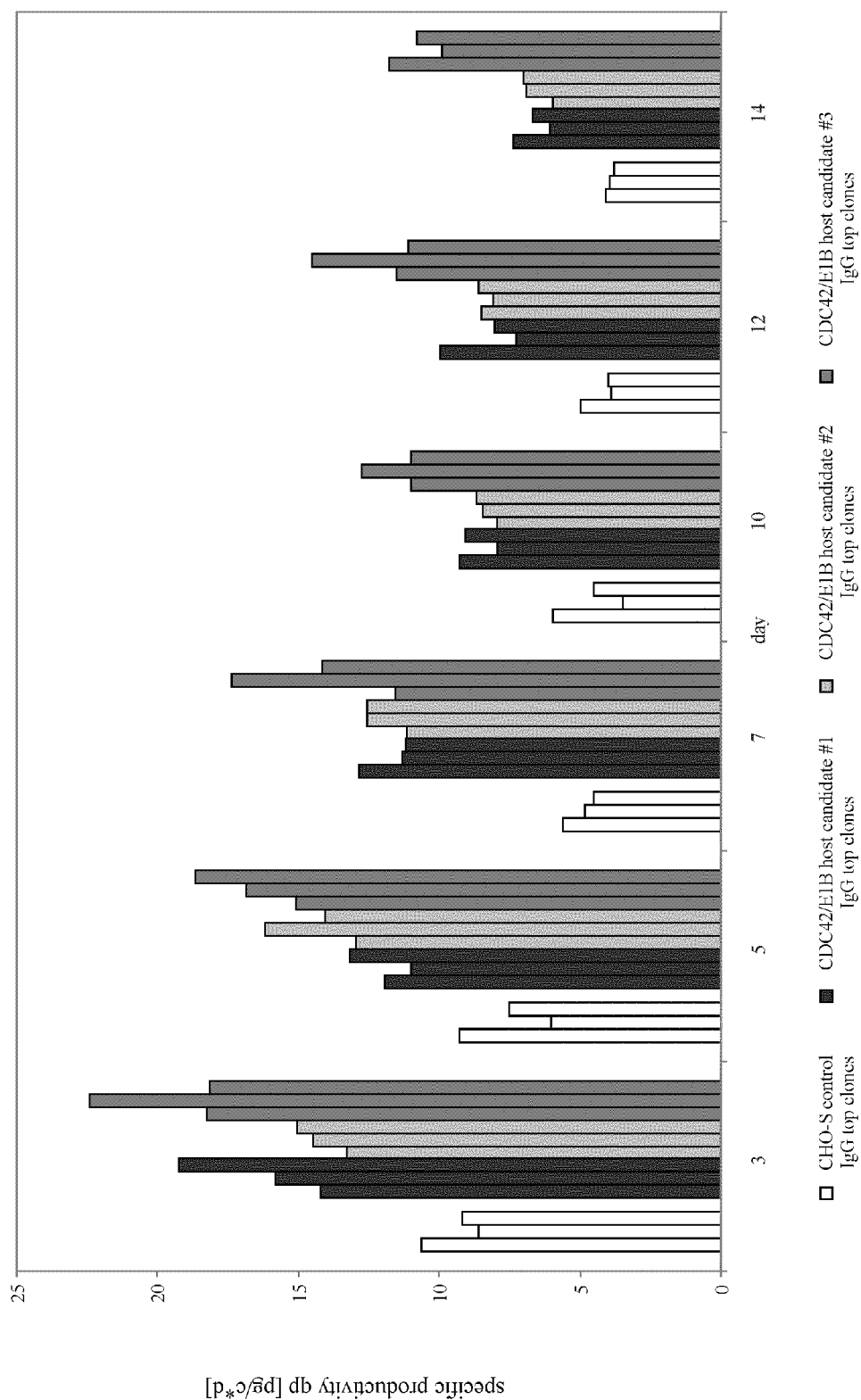
FIG. 10: Shows the specific IgG productivities for the top 3 CHO-S control IgG clones and CDC42F28L/E1B engineered IgG clones in shaken fed-batch culture over 14 days. Abbreviations: CDC42=CDC42F28L fast cycling mutant.

Compared to the clones generated from the parental CHO-S cells the vast majority of the clones derived either from the CDC42F28L and CDC42F28L/E1B starter cell clones displayed higher cell specific productivities (FIG. 9 and FIG. 10). This effect was significantly more pronounced for the CDC42F28L/E1B-derived IgG clones. In addition, the majority of clones derived from engineered starter cell lines (CDC42F28L and CDC42F28L/E1B) produced up to two-fold more product compared to those originating from the parental CHO-S cells (FIG. 7 and FIG. 8).

Consistent with the results shown in Example 1, compared to the unmodified control specific IgG productivity was significantly enhanced in cells where CDC42F28L is constitutively expressed. For engineered cells co-expressing CDC42F28L and E1B specific IgG productivity was even more enhanced. In addition, compared to the unmodified CHO-S control cells, IgG titers were considerably enhanced for engineered cells expressing either CDC42F28L alone or in combination with E1B.

Example 3

The example describes the effect of heterologous CDC42F28L and E1B expression on growth properties and productivity of a pre-existing antibody producer line.
Cell Lines The recombinant cell line CHO-DG44-T was established by stable transfection of the dihydrofolate reductase-deficient CHO cell line, CHO/DG44 with an expression vector PBGA-BEX2 containing expression cassettes comprising nucleotide sequences encoding light and heavy chain of the therapeutic monoclonal antibody Trastuzumab. The cell line has undergone two subsequent cloning rounds ensuring clonality and homogenetity of expression within this clone. Generation of the CDC42F28L/E1B engineered cell lines started from this pre-existing producer clone. The cell line was maintained in serum-free medium C8862 (SAFC).
Engineering of Antibody-Producing CHO-IgG Cells with CDC42/E1B CHO-IgG cells stably expressing the IgG1-type therapeutic antibody Trastuzumab were stably transfected with the expression vector EF2CDC42F28LE1B comprising the CDC42F28L/E1B transgene cassette by electroporation as described above. The cells were co-transfected with the original antibody expression vector. As a control, the very same CHO-IgG cells that have been used to generate CDC42F28L/E1B engineered cell lines were transfected with the original antibody expression vector only. After 24 h transfectants were selected in alpha-MEM containing the antibiotic G418 or puromycin and MTX in the case of the control. The resistant clones were then isolated by limiting dilution cloning as described above. The 20 clones with the highest IgG expression were expanded and adapted to growth in suspension for each, the engineered cells and the control. Those clones were re-analyzed for IgG expression in 24 well plates and top four IgG producers were further expanded for the engineered and control cells.
RT-PCR Analysis for CDC42F28L and E1B Expression For the chosen engineered clones CDC42F28L and E1B expression was confirmed by RT-PCR analysis as described above and confirmed their stable expression.
Production of IgG1 from CDC42F28L/E1B Engineered or Control Cells by Serum-Free Fed-Batch Culture in Shaker Tubes In order to study the effects of CDC42F28L/E1B expression on product titer and specific productivity, the chosen IgG clones were analyzed in parallel shaken fed-batch culture. The engineered and the control cell lines were used to produce IgG1 antibodies in the culture supernatant. Shake flask cultures were inoculated at $4 \times 10^5$ cells/mL in chemically defined culture medium and incubated at 150 rpm, 37° C., 7.5% $pCO_2$. Specific feed was applied every two days and cultures were stopped after 17 days.

Figure 11:
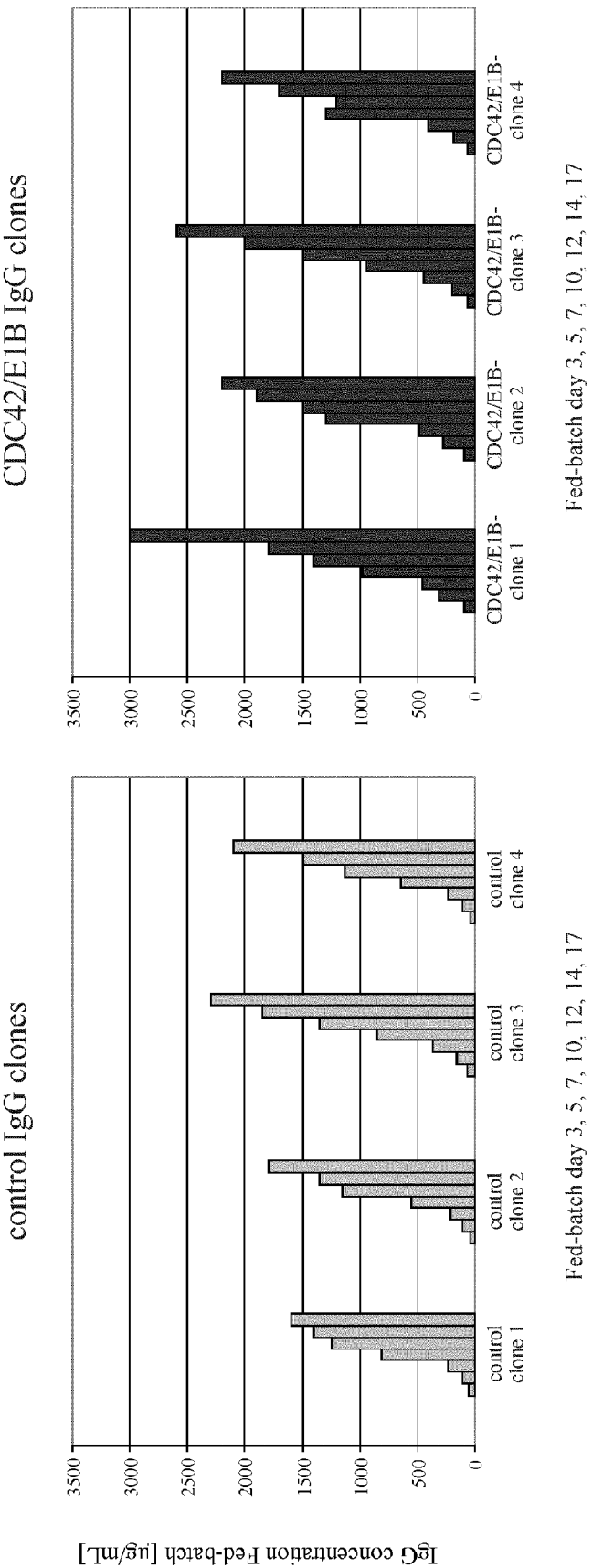
FIG. 11: Shows the cumulative IgG concentrations of the supernatant for the top 4 CHO-DG44-T control clones and CDC42F28L/E1B engineered IgG clones in shaken fed-batch culture over 17 days. Abbreviations: CDC42=CDC42F28L fast cycling mutant.
Figure 12:
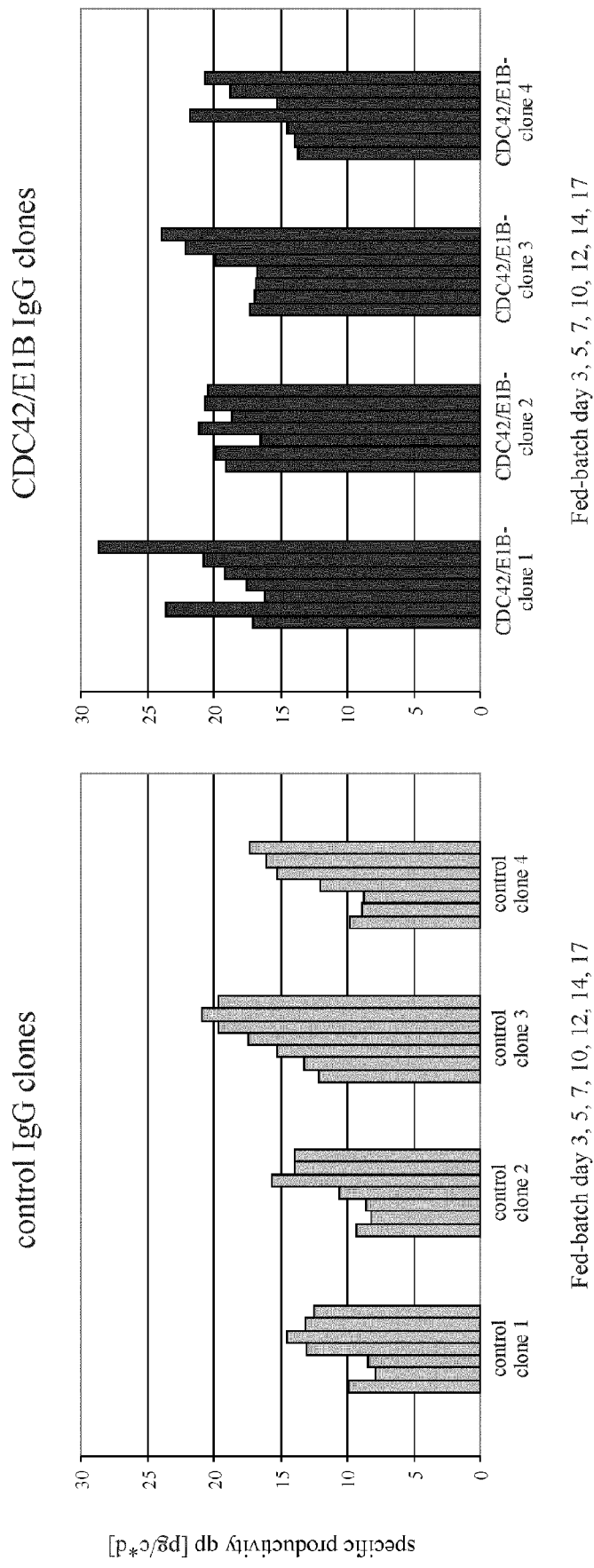
FIG. 12: Shows the specific IgG productivities for the top 4 CHO-DG44-T control clones and CDC42F28L/E1B engineered IgG clones in shaken fed-batch culture over 17 days.

Consistent with the results shown in Example 2 compared to the top CHO-IgG control clones cell specific productivity as well as antibody concentration was substantially higher for the CDC42F28L/E1B engineered top CHO-IgG clones (FIG. 11 and FIG. 12). Consequently, introduction of CDC42F28L in combination with E1B into pre-existing producer clones and its stable expression at various levels results in significantly enhanced antibody expression in a fed-batch process.

The invention claimed is:

1. A non-adherent cell for producing a secreted protein comprising (i) a first polynucleotide comprising a first nucleic acid sequence encoding a fast cycling cdc42 mutant, and (ii) a second polynucleotide comprising a second nucleic acid sequence encoding an exogenous secreted protein, wherein the exogenous secreted protein is an antibody.

2. The cell of claim 1, wherein (i) the fast cycling cdc42 mutant is expressed from a polynucleotide stably maintained in said cell, and (ii) the secreted protein is expressed from a polynucleotide transiently present or stably maintained in said cell.

3. The cell of claim 1, wherein the first nucleic acid sequence encodes
   (i) a fast cycling cdc42 mutant with an amino acid sequence, wherein the amino acid F at amino acid position 28 of SEQ ID NO:8 or at an amino acid position corresponding thereto is replaced by a non-polar amino acid,
   (ii) a fast cycling cdc42 mutant with an amino acid sequence, wherein the amino acid D at amino acid position 118 of SEQ ID NO:8 or at an amino acid position corresponding thereto is replaced by a polar amino acid, or
   (iii) a fast cycling cdc42 mutant with an amino acid sequence, wherein the amino acid F at amino acid position 28 of SEQ ID NO:8 or at an amino acid position corresponding thereto is replaced by a non-polar amino acid and the amino acid D at amino acid position 121 or at an amino acid position corresponding thereto is replaced by a polar amino acid.

4. The cell of claim 3, wherein the first nucleic acid sequence encodes
   (i) a cdc42F28L mutant with an amino acid sequence according to SEQ ID NO: 1 or a variant thereof which is at least 95% identical to said amino acid sequence,
   (ii) a cdc42D118N mutant with an amino acid sequence according to SEQ ID NO: 5 or a variant thereof which is at least 95% identical to said amino acid sequence, or
   (iii) a cdc42F28L/D121N mutant with an amino acid sequence according to SEQ ID NO: 6 or a variant thereof which is at least 95% identical to said amino acid sequence.

5. The cell of claim 3, wherein the first nucleic acid sequence encodes
   (i) a cdc42F28L mutant,
   (ii) a cdc42D118N mutant, or
   (iii) a cdc42F28L/D121N mutant.

6. The cell of claim 5, wherein the first nucleic acid sequence encodes
   (i) a cdc42F28L mutant with an amino acid sequence according to SEQ ID NO: 1 or a variant thereof which is at least 95% identical to said amino acid sequence,
   (ii) a cdc42D118N mutant with an amino acid sequence according to SEQ ID NO: 5 or a variant thereof which is at least 95% identical to said amino acid sequence, or
   (iii) a cdc42F28L/D121N mutant with an amino acid sequence according to SEQ ID NO: 6 or a variant thereof which is at least 95% identical to said amino acid sequence.

7. The cell of claim 1, wherein said cell is further transfected with a polynucleotide comprising an E1B gene region.

8. The cell of claim 7, wherein the E1B gene region is of an Adenovirus from the genus *Mastadenovirus*.

9. The cell of claim 1, wherein said cell is an eukaryotic cell.

10. The cell of claim 9, wherein the eukaryotic cell is a vertebrate cell.

11. The cell of claim 10, wherein the vertebrate cell is a mammalian, fish an amphibian, a reptilian or an avian cell.

12. The cell of claim 11, wherein
    (i) the mammalian cell is a human, hamster, canine or monkey cell,
    (ii) the fish cell is a *Ictalurus punctatus* (channel catfish) cell,
    (iii) the amphibian cell is a *Xenopus laevis* cell,
    (iv) the reptilian cell is an *Iguana iguana* cell, or
    (v) the avian cell is an avian retina cell or an avian somite cell.

13. A method for preparing a non-adherent cell according to claim 1 comprising the following steps:
    (i) providing a non-adherent cell,
    (ii) transfecting said cell with a first polynucleotide comprising a first nucleic acid sequence encoding a fast cycling cdc42 mutant, and
    (iii) transfecting said cell with a second polynucleotide comprising a second nucleic acid sequence encoding an exogenous secreted protein, wherein the exogenous secreted protein is an antibody.

14. The method of claim 13, wherein
    (a) steps (i), (ii), and (iii) are carried out in this order,
    (b) steps (i), (iii) and (ii) are carried out in this order, or
    (c) step (i) is carried out first and steps (ii) and (iii) are carried out next at the same time.

15. A method for producing a secreted protein comprising the following steps:
    (i) providing a non-adherent cell according to claim 1,
    (ii) culturing said cell, and
    (iii) harvesting the exogenous secreted protein produced by said cell.

16. The method of claim 15, wherein harvesting is achieved by separating the exogenous secreted protein from said cell via centrifugation, sedimentation and/or filtration.

17. The method of claim 15, wherein the method further comprises subsequent to step (iii) the step (iv) of purifying the exogenous secreted protein from the cell supernatant.

\* \* \* \* \*

SEQUENCE LISTING

<160> NUMBER OF SEQ ID NOS: 8

<210> SEQ ID NO 1
<211> LENGTH: 191
<212> TYPE: PRT
<213> ORGANISM: Mus musculus

<400> SEQUENCE: 1

Met Gln Thr Ile Lys Cys Val Val Val Gly Asp Gly Ala Val Gly Lys
1               5                   10                  15

Thr Cys Leu Leu Ile Ser Tyr Thr Thr Asn Lys Leu Pro Ser Glu Tyr
            20                  25                  30

Val Pro Thr Val Phe Asp Asn Tyr Ala Val Thr Val Met Ile Gly Gly
        35                  40                  45

Glu Pro Tyr Thr Leu Gly Leu Phe Asp Thr Ala Gly Gln Glu Asp Tyr
    50                  55                  60

Asp Arg Leu Arg Pro Leu Ser Tyr Pro Gln Thr Asp Val Phe Leu Val
65                  70                  75                  80

Cys Phe Ser Val Val Ser Pro Ser Ser Phe Glu Asn Val Lys Glu Lys
                85                  90                  95

Trp Val Pro Glu Ile Thr His His Cys Pro Lys Thr Pro Phe Leu Leu
            100                 105                 110

Val Gly Thr Gln Ile Asp Leu Arg Asp Asp Pro Ser Thr Ile Glu Lys

```
              115                 120                 125
Leu Ala Lys Asn Lys Gln Lys Pro Ile Thr Pro Glu Thr Ala Glu Lys
        130                 135                 140

Leu Ala Arg Asp Leu Lys Ala Val Lys Tyr Val Glu Cys Ser Ala Leu
145                 150                 155                 160

Thr Gln Lys Gly Leu Lys Asn Val Phe Asp Glu Ala Ile Leu Ala Ala
                165                 170                 175

Leu Glu Pro Pro Glu Pro Lys Lys Ser Arg Arg Cys Val Leu Leu
            180                 185                 190

<210> SEQ ID NO 2
<211> LENGTH: 579
<212> TYPE: DNA
<213> ORGANISM: artificial sequence
<220> FEATURE:
<223> OTHER INFORMATION: synthethic codon optimized nucleic acid
      sequence of the CDC42 variant F28L

<400> SEQUENCE: 2
atgcagacca ttaagtgcgt ggtggtcgga gatggcgccg tgggcaagac ctgcctgctg      60
atctcctaca ccaccaacaa gctgccttcc gagtacgtgc ccaccgtgtt cgacaactac     120
gccgtgaccg tgatgatcgg cggcgagcct acaccctgg gcctgttcga caccgctggc     180
caggaagatt acgaccggct gcggcctctg tcttaccctc agaccgacgt gttcctggtc     240
tgcttctccg tggtgtcccc tagctccttc gagaacgtga agaaaaatg gtgcccgag      300 atcacccacc actgccctaa gacccctttc ctgctggtcg cacccagat cgacctgcgg     360 gacgacccct tccaccatcga gaagctggcc aagaacaagc agaagcctat cacccctgag     420
acagccgaaa gctggcccg ggacctgaag gccgtgaaat acgtggagtg ctccgccctg      480
acccagaaag gcctgaagaa cgtgttcgac gaggccatcc tggccgctct ggaacctcct     540
gagcctaaga atcccggcg ctgcgtgctg ctgtgatga                              579

<210> SEQ ID NO 3
<211> LENGTH: 176
<212> TYPE: PRT
<213> ORGANISM: Adenovirus 5

<400> SEQUENCE: 3

Met Glu Ala Trp Glu Cys Leu Glu Asp Phe Ser Ala Val Arg Asn Leu
1               5                   10                  15

Leu Glu Gln Ser Ser Asn Ser Thr Ser Trp Phe Trp Arg Phe Leu Trp
            20                  25                  30

Gly Ser Ser Gln Ala Lys Leu Val Cys Arg Ile Lys Glu Asp Tyr Lys
        35                  40                  45

Trp Glu Phe Glu Glu Leu Leu Lys Ser Cys Gly Glu Leu Phe Asp Ser
    50                  55                  60

Leu Asn Leu Gly His Gln Ala Leu Phe Gln Glu Lys Val Ile Lys Thr
65                  70                  75                  80

Leu Asp Phe Ser Thr Pro Gly Arg Ala Ala Ala Val Ala Phe Leu
                85                  90                  95

Ser Phe Ile Lys Asp Lys Trp Ser Glu Glu Thr His Leu Ser Gly Gly
            100                 105                 110

Tyr Leu Leu Asp Phe Leu Ala Met His Leu Trp Arg Ala Val Val Arg
        115                 120                 125

His Lys Asn Arg Leu Leu Leu Ser Ser Val Arg Pro Ala Ile Ile
    130                 135                 140
```

```
Pro Thr Glu Glu Gln Gln Gln Gln Glu Glu Ala Arg Arg Arg Arg
145                 150                 155                 160

Gln Glu Gln Ser Pro Trp Asn Pro Arg Ala Gly Leu Asp Pro Arg Glu
            165                 170                 175
```

<210> SEQ ID NO 4
<211> LENGTH: 496
<212> TYPE: PRT
<213> ORGANISM: Adenovirus 5

<400> SEQUENCE: 4

```
Met Glu Arg Arg Asn Pro Ser Glu Arg Gly Val Pro Ala Gly Phe Ser
1               5                   10                  15

Gly His Ala Ser Val Glu Ser Gly Cys Glu Thr Gln Glu Ser Pro Ala
            20                  25                  30

Thr Val Val Phe Arg Pro Pro Gly Asp Asn Thr Asp Gly Gly Ala Ala
        35                  40                  45

Ala Ala Ala Gly Gly Ser Gln Ala Ala Ala Gly Ala Glu Pro Met
50                  55                  60

Glu Pro Glu Ser Arg Pro Gly Pro Ser Gly Met Asn Val Val Gln Val
65                  70                  75                  80

Ala Glu Leu Tyr Pro Glu Leu Arg Arg Ile Leu Thr Ile Thr Glu Asp
                85                  90                  95

Gly Gln Gly Leu Lys Gly Val Lys Arg Glu Arg Gly Ala Cys Glu Ala
            100                 105                 110

Thr Glu Glu Ala Arg Asn Leu Ala Phe Ser Leu Met Thr Arg His Arg
        115                 120                 125

Pro Glu Cys Ile Thr Phe Gln Gln Ile Lys Asp Asn Cys Ala Asn Glu
130                 135                 140

Leu Asp Leu Leu Ala Gln Lys Tyr Ser Ile Glu Gln Leu Thr Thr Tyr
145                 150                 155                 160

Trp Leu Gln Pro Gly Asp Asp Phe Glu Glu Ala Ile Arg Val Tyr Ala
                165                 170                 175

Lys Val Ala Leu Arg Pro Asp Cys Lys Tyr Lys Ile Ser Lys Leu Val
            180                 185                 190

Asn Ile Arg Asn Cys Cys Tyr Ile Ser Gly Asn Gly Ala Glu Val Glu
        195                 200                 205

Ile Asp Thr Glu Asp Arg Val Ala Phe Arg Cys Ser Met Ile Asn Met
210                 215                 220

Trp Pro Gly Val Leu Gly Met Asp Gly Val Val Ile Met Asn Val Arg
225                 230                 235                 240

Phe Thr Gly Pro Asn Phe Ser Gly Thr Val Phe Leu Ala Asn Thr Asn
                245                 250                 255

Leu Ile Leu His Gly Val Ser Phe Tyr Gly Phe Asn Asn Thr Cys Val
            260                 265                 270

Glu Ala Trp Thr Asp Val Arg Val Arg Gly Cys Ala Phe Tyr Cys Cys
        275                 280                 285

Trp Lys Gly Val Val Cys Arg Pro Lys Ser Arg Ala Ser Ile Lys Lys
290                 295                 300

Cys Leu Phe Glu Arg Cys Thr Leu Gly Ile Leu Ser Glu Gly Asn Ser
305                 310                 315                 320

Arg Val Arg His Asn Val Ala Ser Asp Cys Gly Cys Phe Met Leu Val
                325                 330                 335

Lys Ser Val Ala Val Ile Lys His Asn Met Val Cys Gly Asn Cys Glu
```

```
                    340                 345                 350
Asp Arg Ala Ser Gln Met Leu Thr Cys Ser Asp Gly Asn Cys His Leu
                355                 360                 365
Leu Lys Thr Ile His Val Ala Ser His Ser Arg Lys Ala Trp Pro Val
            370                 375                 380
Phe Glu His Asn Ile Leu Thr Arg Cys Ser Leu His Leu Gly Asn Arg
385                 390                 395                 400
Arg Gly Val Phe Leu Pro Tyr Gln Cys Asn Leu Ser His Thr Lys Ile
                405                 410                 415
Leu Leu Glu Pro Glu Ser Met Ser Lys Val Asn Leu Asn Gly Val Phe
            420                 425                 430
Asp Met Thr Met Lys Ile Trp Lys Val Leu Arg Tyr Asp Glu Thr Arg
            435                 440                 445
Thr Arg Cys Arg Pro Cys Glu Cys Gly Lys His Ile Arg Asn Gln
                450                 455                 460
Pro Val Met Leu Asp Val Thr Glu Leu Arg Pro Asp His Leu Val
465                 470                 475                 480
Leu Ala Cys Thr Arg Ala Glu Phe Gly Ser Ser Asp Glu Asp Thr Asp
                485                 490                 495

<210> SEQ ID NO 5
<211> LENGTH: 191
<212> TYPE: PRT
<213> ORGANISM: Mus musculus

<400> SEQUENCE: 5

Met Gln Thr Ile Lys Cys Val Val Gly Asp Gly Ala Val Gly Lys
1               5                   10                  15
Thr Cys Leu Leu Ile Ser Tyr Thr Thr Asn Lys Phe Pro Ser Glu Tyr
            20                  25                  30
Val Pro Thr Val Phe Asp Asn Tyr Ala Val Thr Val Met Ile Gly Gly
        35                  40                  45
Glu Pro Tyr Thr Leu Gly Leu Phe Asp Thr Ala Gly Gln Glu Asp Tyr
    50                  55                  60
Asp Arg Leu Arg Pro Leu Ser Tyr Pro Gln Thr Asp Val Phe Leu Val
65                  70                  75                  80
Cys Phe Ser Val Val Ser Pro Ser Ser Phe Glu Asn Val Lys Glu Lys
                85                  90                  95
Trp Val Pro Glu Ile Thr His His Cys Pro Lys Thr Pro Phe Leu Leu
            100                 105                 110
Val Gly Thr Gln Ile Asn Leu Arg Asp Asp Pro Ser Thr Ile Glu Lys
        115                 120                 125
Leu Ala Lys Asn Lys Gln Lys Pro Ile Thr Pro Glu Thr Ala Glu Lys
    130                 135                 140
Leu Ala Arg Asp Leu Lys Ala Val Lys Tyr Val Glu Cys Ser Ala Leu
145                 150                 155                 160
Thr Gln Lys Gly Leu Lys Asn Val Phe Asp Glu Ala Ile Leu Ala Ala
                165                 170                 175
Leu Glu Pro Pro Glu Pro Lys Lys Ser Arg Arg Cys Val Leu Leu
            180                 185                 190

<210> SEQ ID NO 6
<211> LENGTH: 191
<212> TYPE: PRT
<213> ORGANISM: Mus musculus
```

<400> SEQUENCE: 6

| | | | | | | | | | | | | | | | |
|---|---|---|---|---|---|---|---|---|---|---|---|---|---|---|---|
|Met|Gln|Thr|Ile|Lys|Cys|Val|Val|Gly|Asp|Gly|Ala|Val|Gly|Lys| |
|1| | | |5| | | | |10| | | | |15| |

Thr Cys Leu Leu Ile Ser Tyr Thr Thr Asn Lys Leu Pro Ser Glu Tyr
            20                  25                  30

Val Pro Thr Val Phe Asp Asn Tyr Ala Val Thr Val Met Ile Gly Gly
        35                  40                  45

Glu Pro Tyr Thr Leu Gly Leu Phe Asp Thr Ala Gly Gln Glu Asp Tyr
    50                  55                  60

Asp Arg Leu Arg Pro Leu Ser Tyr Pro Gln Thr Asp Val Phe Leu Val
65              70                  75                  80

Cys Phe Ser Val Val Ser Pro Ser Ser Phe Glu Asn Val Lys Glu Lys
                85                  90                  95

Trp Val Pro Glu Ile Thr His His Cys Pro Lys Thr Pro Phe Leu Leu
                100                 105                 110

Val Gly Thr Gln Ile Asp Leu Arg Asn Asp Pro Ser Thr Ile Glu Lys
            115                 120                 125

Leu Ala Lys Asn Lys Gln Lys Pro Ile Thr Pro Glu Thr Ala Glu Lys
    130                 135                 140

Leu Ala Arg Asp Leu Lys Ala Val Lys Tyr Val Glu Cys Ser Ala Leu
145                 150                 155                 160

Thr Gln Lys Gly Leu Lys Asn Val Phe Asp Glu Ala Ile Leu Ala Ala
                165                 170                 175

Leu Glu Pro Pro Glu Pro Lys Lys Ser Arg Arg Cys Val Leu Leu
                180                 185                 190

<210> SEQ ID NO 7
<211> LENGTH: 1798
<212> TYPE: DNA
<213> ORGANISM: Adenovirus 5

<400> SEQUENCE: 7

| | | |
|---|---|---|
|atggaggctt gggagtgttt ggaagatttt tctgctgtgc gtaacttgct ggaacagagc|60|
|tctaacagta cctcttggtt ttggaggttt ctgtggggct catcccaggc aaagttagtc|120|
|tgcagaatta aggaggatta caagtgggaa tttgaagagc ttttgaaatc ctgtggtgag|180|
|ctgtttgatt ctttgaatct gggtcaccag gcgcttttcc aagagaaggt catcaagact|240|
|ttggattttt ccacaccggg gcgcgctgcg gctgctgttg ctttttttgag ttttataaag|300|
|gataaatgga gcgaagaaac ccatctgagc gggggggtacc tgctggattt tctgccatg|360|
|catctgtgga gagcggttgt gagacacaag aatcgcctgc tactgttgtc ttccgtccgc|420|
|ccggcgataa taccgacgga ggagcagcag cagcagcagg aggaagccag gcggcggcgg|480|
|caggagcaga gcccatggaa cccgagagcc ggcctggacc ctcgggaatg aatgttgtac|540|
|aggtggctga actgtatcca gaactgagac gcattttgac aattacagag gatgggcagg|600|
|ggctaaaggg ggtaaagagg gagcgggggg cttgtgaggc tacagaggag ctaggaatc|660|
|tagcttttag cttaatgacc agacaccgtc ctgagtgtat tacttttcaa cagatcaagg|720|
|ataattgcgc taatgagctt gatctgctgg cgcagaagta ttccatagag cagctgacca|780|
|cttactggct gcagccaggg gatgattttg aggaggctat tagggtatat gcaaggtgg|840|
|cacttaggcc agattgcaag tacaagatca gcaaacttgt aaatatcagg aattgttgct|900|
|acatttctgg gaacggggcc gaggtggaga tagatacgga ggataggtg gcctttagat|960|
|gtagcatgat aaatatgtgg ccggggggtgc ttggcatgga cggggtggtt attatgaatg|1020|

```
taaggtttac tggccccaat tttagcggta cggttttcct ggccaatacc aaccttatcc    1080
tacacggtgt aagcttctat gggtttaaca atacctgtgt ggaagcctgg accgatgtaa    1140
gggttcgggg ctgtgccttt tactgctgct ggaaggggggt ggtgtgtcgc cccaaaagca   1200
gggcttcaat taagaaatgc ctctttgaaa ggtgtacctt gggtatcctg tctgagggta    1260
actccagggt gcgccacaat gtggcctccg actgtggttg cttcatgcta gtgaaaagcg    1320
tggctgtgat taagcataac atggtatgtg caactgcga ggacagggcc tctcagatgc     1380
tgacctgctc ggacggcaac tgtcacctgc tgaagaccat tcacgtagcc agccactctc    1440
gcaaggcctg gccagtgttt gagcataaca tactgacccg ctgttccttg catttgggta    1500
acaggagggg ggtgttccta ccttaccaat gcaatttgag tcacactaag atattgcttg    1560
agcccgagag catgtccaag gtgaacctga acggggtgtt tgacatgacc atgaagatct    1620
ggaaggtgct gaggtacgat gagacccgca ccaggtgcag accctgcgag tgtggcggta    1680
aacatattag gaaccagcct gtgatgctgg atgtgaccga ggagctgagg cccgatcact    1740
tggtgctggc ctgcacccgc gctgagtttg gctctagcga tgaagataca gattgagg     1798
```

```
<210> SEQ ID NO 8
<211> LENGTH: 191
<212> TYPE: PRT
<213> ORGANISM: Mus musculus

<400> SEQUENCE: 8

Met Gln Thr Ile Lys Cys Val Val Val Gly Asp Gly Ala Val Gly Lys
1               5                   10                  15

Thr Cys Leu Leu Ile Ser Tyr Thr Thr Asn Lys Phe Pro Ser Glu Tyr
                20                  25                  30

Val Pro Thr Val Phe Asp Asn Tyr Ala Val Thr Val Met Ile Gly Gly
            35                  40                  45

Glu Pro Tyr Thr Leu Gly Leu Phe Asp Thr Ala Gly Gln Glu Asp Tyr
        50                  55                  60

Asp Arg Leu Arg Pro Leu Ser Tyr Pro Gln Thr Asp Val Phe Leu Val
65                  70                  75                  80

Cys Phe Ser Val Val Ser Pro Ser Ser Phe Glu Asn Val Lys Glu Lys
                85                  90                  95

Trp Val Pro Glu Ile Thr His His Cys Pro Lys Thr Pro Phe Leu Leu
                100                 105                 110

Val Gly Thr Gln Ile Asp Leu Arg Asp Asp Pro Ser Thr Ile Glu Lys
            115                 120                 125

Leu Ala Lys Asn Lys Gln Lys Pro Ile Thr Pro Glu Thr Ala Glu Lys
        130                 135                 140

Leu Ala Arg Asp Leu Lys Ala Val Lys Tyr Val Glu Cys Ser Ala Leu
145                 150                 155                 160

Thr Gln Lys Gly Leu Lys Asn Val Phe Asp Glu Ala Ile Leu Ala Ala
                165                 170                 175

Leu Glu Pro Pro Glu Pro Lys Lys Ser Arg Arg Cys Val Leu Leu
                180                 185                 190
```